US008603309B2

(12) United States Patent
Cai et al.

(10) Patent No.: US 8,603,309 B2
(45) Date of Patent: Dec. 10, 2013

(54) DISPOSABLE SENSOR FOR ELECTROCHEMICAL DETECTION OF HEMOGLOBIN

(75) Inventors: Xiaohua Cai, Needham, MA (US); Chung Chang Young, Weston, MA (US); Jessica Joy Mokfienski, Cambridge, MA (US)

(73) Assignee: Nova Biomedical Corporation, Waltham, MA (US)

( * ) Notice: Subject to any disclaimer, the term of this patent is extended or adjusted under 35 U.S.C. 154(b) by 0 days.

(21) Appl. No.: 13/230,423

(22) Filed: Sep. 12, 2011

(65) Prior Publication Data
US 2013/0062221 A1     Mar. 14, 2013

(51) Int. Cl.
*G01N 27/327*     (2006.01)
(52) U.S. Cl.
USPC ............... 204/403.04; 204/403.01; 205/777.5
(58) Field of Classification Search
USPC ............. 204/403.01–403.15, 412; 205/777.5, 205/778, 792; 422/82.01, 82.02
See application file for complete search history.

(56) References Cited

U.S. PATENT DOCUMENTS

| 4,876,205 A | 10/1989 | Green et al. .................... 436/66 |
| 5,565,085 A | 10/1996 | Ikeda et al. .................. 205/777.5 |
| 5,582,697 A | 12/1996 | Ikeda et al. .................. 205/777.5 |
| 5,582,698 A | 12/1996 | Flaherty et al. ........... 204/403.09 |
| 5,672,256 A | 9/1997 | Yee ............................. 422/82.01 |
| 5,708,247 A | 1/1998 | McAleer et al. ......... 204/403.05 |
| 5,773,301 A | 6/1998 | Ziegler ............................ 436/66 |
| 5,791,344 A | 8/1998 | Schulman et al. ............. 600/347 |
| 5,866,428 A | 2/1999 | Kim et al. |
| 5,882,934 A | 3/1999 | Li et al. ............................ 436/66 |
| 5,951,836 A | 9/1999 | McAleer et al. ............ 205/777.5 |
| 5,958,781 A | 9/1999 | Wong et al. ...................... 436/63 |
| 6,241,862 B1 | 6/2001 | McAleer et al. |
| 6,258,229 B1 | 7/2001 | Winarta et al. ........... 204/403.04 |
| 6,284,125 B1 | 9/2001 | Hodges et al. ................. 205/775 |
| 6,287,451 B1 | 9/2001 | Winarta et al. ............. 205/777.5 |
| 6,413,410 B1 | 7/2002 | Hodges et al. ................. 205/775 |
| 6,632,349 B1 | 10/2003 | Hodges et al. ................. 205/792 |
| 6,733,655 B1 | 5/2004 | Davies et al. .................. 205/775 |
| 6,767,441 B1 | 7/2004 | Cai et al. .................. 204/403.03 |
| 6,837,976 B2 | 1/2005 | Cai et al. .................. 204/403.14 |

(Continued)

FOREIGN PATENT DOCUMENTS

EP     0 256 851     2/1988
JP     63-101745     5/1988

(Continued)

OTHER PUBLICATIONS

G. Vanzetti, "An azide-methemoglobin method for hemoglobin determination in blood", *J. Lab. Clin. Med.*, pp. 116-126 (1966).
W. Stadie, "The Oxygen of the Arterial and Venous Blood in Pneumonia and its Relation to Cyanosis", *J. Biol. Chem.*, pp. 215-241 (1920).

(Continued)

*Primary Examiner* — J. Christopher Ball
(74) *Attorney, Agent, or Firm* — Ostrolenk Faber LLP

(57) ABSTRACT

A disposable biosensor for determining the content of hemoglobin and hematocrit in a sample of whole blood that includes a laminated strip with a first and second end, at least a reference, a working electrode and a blank electrode embedded in the laminated strip. The working electrode contains a reagent sensitive to hemoglobin or hemotocrit. The blank electrode is used to measure oxidizable species in the fluid sample and to correct the current signal of the working electrode. The construction of the biosensor allows accurate measurement of the impedance of a small fluid sample, which is used to further correct the current signal of the working electrode.

39 Claims, 12 Drawing Sheets

(56) References Cited

U.S. PATENT DOCUMENTS

| | | |
|---|---|---|
| 6,942,770 B2 | 9/2005 | Cai et al. .................. 204/403.04 |
| 7,112,265 B1 | 9/2006 | McAleer et al. ......... 204/403.09 |
| 7,250,105 B1 | 7/2007 | Davies et al. .............. 205/777.5 |
| 7,337,918 B2 | 3/2008 | Fowler et al. .................... 221/65 |
| 7,648,624 B2 | 1/2010 | Cai et al. ....................... 205/782 |
| RE41,264 E | 4/2010 | Cai et al. .................. 204/403.03 |
| 7,727,167 B2 | 6/2010 | Fowler et al. ................. 600/583 |
| 7,749,766 B2 | 7/2010 | Pei et al. .......................... 436/97 |
| 7,955,484 B2 | 6/2011 | Cai et al. .................. 204/403.04 |
| 2003/0082076 A1 | 5/2003 | Lin et al. |
| 2003/0201177 A1 | 10/2003 | Hodges et al. ........... 204/403.01 |
| 2004/0081752 A1 | 4/2004 | Lin et al. |
| 2006/0278537 A1 | 12/2006 | Cai et al. ..................... 205/777.5 |
| 2007/0062822 A1 | 3/2007 | Fujiwara et al. .............. 205/792 |
| 2007/0131549 A1 | 6/2007 | Cai et al. .................. 204/403.02 |
| 2008/0223732 A1 | 9/2008 | Hodges et al. |
| 2009/0104641 A1 | 4/2009 | Su et al. |
| 2011/0192731 A1 | 8/2011 | Bhattacharya |

FOREIGN PATENT DOCUMENTS

| | | |
|---|---|---|
| JP | 2005-114359 | 4/2005 |
| JP | 2005-523443 | 8/2005 |
| JP | 2007-163299 | 6/2007 |
| JP | 2007-271622 | 10/2007 |
| JP | 2007-537456 | 12/2007 |
| JP | 2008-76143 | 4/2008 |
| JP | 2009-168815 | 7/2009 |
| JP | 2010-2401 | 1/2010 |
| WO | WO 03/089658 A1 | 10/2003 |
| WO | WO 2005/114164 | 12/2005 |

OTHER PUBLICATIONS

C. Burtis et al., *Tietz Textbook of Clinical Chemistry*, (1996).

D. Drabkin et al., "Spectrophotometric Studies", *J. Biol. Chem.*, pp. 719-733 (1932).

S. Morris et al, "Precision, accuracy, and reliability of hemoglobin assessment with use of capillary blood[1-4]", *Am. J. Clin. Nutr.*, pp. 1243-1248 (1999).

H. Gehring et al., "Accuracy of point-of-care-testing (POCT) for determining hemoglobin concentrations", *Acta Anaesthesol Scand.*, 46:980-986 (2002).

AJ Mighell et al., "Histological identification of carcinoma in 21 gauge need tracks after fine needle aspiration biopsy of head and neck carcinoma", *J. Clin. Pathol.*, 51:241-252 (2007).

S. Hopfer et al., "Effect of Protein on Hemoglobin and Hematocrit Assays with a Conductivity-Based Point-of-Care Testing Device: Comparison with Optical Methods", *Annals of Clinical & Laboratory Science*, 34(1):75-82 (2004).

International Search Report and Written Opinion dated Nov. 16, 2012 in corresponding International Application No. PCT/US2012/053851.

Nijboer et al., "Myth or Reality Hematcrit and Hemoglobin Biffer Trauma." J. Trauma. 2007; 62(5): 1310-2 (2007), p. 106-110.

European Search Report and Preliminary Opinion dated Dec. 7, 2012 issued in corresponding European Application No. 12183540.

Liying Jiang et al., "Disposable Biosensor for Memoglobin Determination in Whole Blood" Nano/Micro Engineered and Molecular System, 2006. NEMS '06. 1st IEEE International Conference on, IEEE, PI, Jan. 1, 2006, pp. 204-208, XP031063830, ISBN: 978-1-4244-0139-0.

Japanese Office Action dated Oct. 1, 2013 issued in corresponding Japanese Application No. 2012-199212 (including English translation).

DISPOSABLE SENSOR FOR ELECTROCHEMICAL DETECTION OF HEMOGLOBIN

FIELD OF THE INVENTION

The present invention relates generally to electrochemical sensors that can be used for the quantification of a specific component or analyte in a liquid sample. Particularly, the present invention relates to a disposable electrochemical sensor for measuring hemoglobin concentration in blood. More particularly, the present invention relates to a system for simultaneously measuring hemoglobin and hemotocrit in a blood sample. Still more particularly, the present invention relates to a device that can be employed to perform assays of hemoglobin and hemotocrit in a small volume sample (around 1.6 µL) with high accuracy.

DESCRIPTION OF THE PRIOR ART

Hemoglobin is a protein inside red blood cells that carries oxygen throughout the body. A hemoglobin test reveals how much hemoglobin is in a person's blood, which can be used to diagnose and monitor anemia (a low hemoglobin level) and polycythemia vera (a high hemoglobin level). A low hemoglobin measurement usually means the person has anemia. An elevated hemoglobin may be caused by dehydration (decreased water), hypoxia (decreased oxygen), or polycythemia cera.

The hemoglobin measurement in venous or capillary blood is one of the most frequently performed clinical analyses. In trauma cases, operating rooms and intensive care units, it is essential to know the patient's hemoglobin value immediately. Hemoglobin is used to monitor and manage anemia in dialysis patients. It is also a widely used parameter to screen blood donors for anemia in blood banks. Therefore, accurate measurement of hemoglobin is highly desirable.

Colorimetric methods are the most popular methods for the measurement of hemoglobin. These methods rely on the reduction property of the ferrous iron of hemoglobin, HbFe(II) (Ashwood, R. Edward and Burtis, A. Carl. *Tietz Textbook of Clinical Chemistry*. 1996; W. C. Stadie, *J. Biol. Chem.*, 1920, 41, 237). Specifically, the ferrous iron of hemoglobin is oxidized by an oxidant, e.g. ferricyanide, to produce HbFe(III), a methemoglobin monomer, which is then converted to a stable cyanmethemoglobin by addition of potassium cyanide. The absorbance of the resulted cyanmethemoglobin, measured photometrically, is related to the hemoglobin concentration. This method has been modified by the use of Drabkin's reagent (Drabkin et al. J. Biol. Chem. 1932, 98, 719) which comprises an alkaline aqueous solution of potassium ferricyanide and potassium cyanide and thus allows the assay to be performed using a single reagent. Vanzetti in J. Lab. Clin. Med. 1966, 67, 116 has proposed using sodium azide in place of potassium cyanide. The azide-methaemoglobin has a similar absorption spectrum to that of cyanomethaemoglobin. Because of toxicity of potassium cyanide, the methods were improved later by several groups (S. Wong et al., U.S. Pat. No. 5,958,781; Y. Li et al., U.S. Pat. No. 5,882,934; W. Ziegler, U.S. Pat. No. 5,773,301) to achieve cyanide free reagents. A few products have been developed and marketed based on the improvements.

The BIOSAFE Anemia Meter (Biosafe Co., Pittsburg, Pa.) is considered the first instant blood test for the detection of anemia. The method relies on the blood (a few drops of blood needed) movement and color development (15-25 min) in the device, and the result is read by naked eyes from the scale.

The STAT—Site® MHgb Test System (Stanbio Laboratory Co., Boerne, Tex.) consists of a reflectance meter and a hemoglobin test card that measures hemoglobin in a single drop of blood. The reaction is based on the azidemethemoglobin method and uses either finger stick or venous whole blood samples (about 10 µl, blood needed).

HemoCue system (HemoCue Inc., Cypress, Calif.) is widely used currently for measuring hemoglobin in whole blood. Approximately 10 µL of blood is taken to fill up capillary cuvette containing a reagent consisting of sodium deoxycholate, sodium nitrite, and sodium azide nitrite reagent, which lyses the blood and converts the hemoglobin to hemiglobinazide. The absorbance is then measured spectrometrically (S. S. Morris, et al., *Am. J. Clin. Nutr.*, 1999, 69(6), 1243). Because of the problems associated with the spectrometric measurement systems, like cuvette fillings and background turbidity and other issues (e.g. bubble trap), wide scattering results were reported (H. Gehring et al., *Acta Anaes. Scand.*, 2002, 46, 980). A.M. Conway et al. warned that the measurement of hemoglobin from single drops of skin puncture blood with the HemoCue system should be discontinued. (*J. Clin. Pathol.*, 1998, 51, 248).

The iSTAT-1 POCT device (Model iSTAT-1 with EC6+ cartridges, I-STAT Corp., Princeton, N.J.) uses a conductivity-based method to measure blood hematocrit. The measured conductivity is reversely related to the hematocrit concentration in the blood samples. The blood hemoglobin concentration is calculated through an experiential equation. It is obvious that the conductivity can be strongly influenced by plasma protein concentration and electrolyte concentration and other factors. The results would be highly dubious considering varying plasma protein concentration and electrolyte (for example, sodium chloride) concentration in the blood samples. Therefore, it is recommended that hemotocrit and hemoglobin testing in patients with suspected hypoproteinemia or substantial hemodilution should be tested with a non conductivity-based method (Sidney M. Hopfer et al., *Annals of Clinical & Laboratory Science*, 2004, 34, 75.)

Electrochemical techniques have received much attention in recent years due to their advantages like rapidity, high sensitivity, cheap instrumentation and simple operation. J. Green, et al. disclosed an electrochemical assay for hemoglobin in U.S. Pat. No. 4,876,205. The method is based on the use of a dry strip loaded with a mixture comprising a surfactant (to lyse red cell and release hemoglobin), potassium ferricyanide (to oxidize HbFe(II)) of hemoglobin). After 30-60 s incubation in 20 µL of blood sample, current-time transients are recorded (amperometry) with an applied potential of 0.45V or 0.50V vs. Ag/AgCl reference electrode and the currents, measured after 30 s, are related to the hemoglobin concentration in the blood samples.

Based on the above potassium ferricyanide-HbFe(II) reaction principle, A. Hodges, et al., disclosed a disposable electrochemical cell in U.S. Pat. No. 6,632,349 and US Patent Application 20030201177 for the detection of hemoglobin concentration. The disposable electrochemical cell was constructed having a sensing chamber, a first electrode and a second electrode (reference electrode) wherein the second electrode is mounted in opposing relationship (face to face) with a distance of less than 500 microns from the first electrode. The sensing cell is operated as an amperometric sensor.

Recently, a U.S. patent application Ser. No. 20070062822 disclosed an electrochemical sensor for measuring hemotocrit. The disclosed method provides an electrode system having a working electrode and a counter electrode, a redox substance being provided on the counter electrode but not on the working electrode. A high voltage (equal or higher than a voltage causing electrolysis of water) is applied across the electrode system. According to the data disclosed in the patent, the hematocrit concentration is also reversely proportional to the resulting current signal.

More recently, a U.S. patent application Ser. No. 20090104641 disclosed an electrochemical method and a test strip for detecting hemoglobin in a specimen. The method is based on detecting electric current produced by the reaction of the hemoglobin and an electron mediator (tetrathiafulvalene or dimethylferrocene modified by cyclodextrin) in a specimen under a potentiostatic condition. However, the hemoglobin concentration is in reverse proportion to the current signal, that is, a lower hemoglobin concentration or hematocrit gives a higher current response, or vice versa.

It is highly desirable to measure hemoglobin and hematocrit accurately. A falsely high or low hemoglobin test result will result in wrongful treatments for patients, even leading to life-threatening complications. Therefore, it is desirable to have a hemoglobin measuring system that can provide a more accurate hemoglobin reading.

Furthermore, it is desirable to have a hemoglobin measuring system that can provide a more accurate hemoglobin reading by overcoming the deficiencies of the prior art methods caused by varying factors.

Moreover, it is desirable to have an electrochemical sensor that requires less sample volume than previously required by the prior art.

It is also desirable to have a disposable, user-friendly hemoglobin sensor capable of providing more accurate hemoglobin readings.

SUMMARY OF THE INVENTION

It is an object of the present invention to provide a disposable hemoglobin sensor capable of measuring the hemoglobin concentration in a small volume of body fluid.

It is another object of the present invention to provide a disposable hemoglobin sensor that is capable of measuring the hemoglobin concentration in a small volume of body fluid such as blood obtained by lancing the skin of the user.

It is a further object of the present invention to provide a disposable hemoglobin sensor that has a fast response time.

It is yet another object of the present invention to provide a disposable sensor for use in determining hemoglobin and hemotocrit simultaneously in a blood sample with a single disposable device.

It is a further object of the present invention to provide methods for reliable measurement of the hemoglobin content in a blood sample using a sensor strip.

The present invention provides these and other objectives in the following described embodiments.

According to one embodiment of the present invention a sensor strip is configured for hemoglobin measurements in a whole blood sample and includes a base layer having at least a first electrically conductive layer and a second electrically conductive layer disposed on a surface thereof; a first amount of a reagent composition that includes at least an effective amount of a hemoglobin sensitive redox mediator in contact with the first electrically conductive layer to define a working electrode and a second amount of a reagent composition in contact with the second electrically conductive layer to define a reference electrode; and a channel providing communication between the first amount and the second amount of reagent composition; wherein the sensor strip returns a measurable electrical signal indicative of the hemoglobin content of a blood sample in response to an independent application of a variable voltage and a constant voltage across the working electrode and the reference electrode when the blood sample is in contact with the first and second amount of reagent composition inside the channel.

According to one aspect of the present invention the redox mediator oxidizes hemoglobin iron (II), and in one embodiment may be potassium ferricyanide comprising 0.1% to 20% (W/W) of the reagent composition.

According to another aspect of the present invention the reagent composition further comprises an effective amount of a polymer binder, an effective amount of surfactant and at least one buffer. The polymer binder may be in the range 0.04% to 2% (W/W) of the composition, the surfactant may be in the range 0.01% to 5% (W/W) of the composition and the buffer may have a pH above 7. The polymer binder may comprise polyethylene oxide, the surfactant may comprise a polyoxyethylene ether and the buffer may comprise an alkaline composition.

In one preferred embodiment, the sensor strip may include a first middle layer over the base layer, a second middle layer over the first middle layer and a top layer, the first middle layer including a first opening that registers with the first conductive layer in which the reagent composition is received and a second opening that registers with the second conductive layer in which the reagent composition is received, the second middle layer including a cut away residing above the first and the second openings to define the channel, and the top layer including a vent opening in communication with the channel, wherein the channel is sized to receive no more than 2 micro liters of whole blood according to another aspect of the present invention.

According to another embodiment of the present invention, the sensor strip further includes a third electrically conductive layer on the base layer and a second reagent composition in contact with the third conductive layer to define a blank electrode, the third reagent composition including a hemoglobin insensitive redox mediator. In this embodiment, the first middle layer includes a first through opening that registers with the first conductive layer in which the reagent composition is received, a second through opening that registers with the second conductive layer in which the reagent composition is received and a third opening that registers with the third conductive layer in which the second reagent composition is received, the second middle layer including a cut away residing above the first, the second and the third openings to define the channel, and the top layer including a vent opening in communication with the channel, wherein the channel is sized to receive no more than 2 micro liters of whole blood according to an aspect of the present invention.

In one embodiment, the reagent composition in contact with the second electrically conductive layer comprises an Ag/AgCl stack instead of the redox mediator.

According to another aspect of the present invention the blood sample may have a volume in the range of 1.6 micro liter to 10 micro liter.

In another embodiment, the first amount of the first reagent composition and the second amount of the second reagent composition are identical compositions.

According to another embodiment, a sensor strip is configured for hemoglobin measurements in a whole blood sample and includes a base layer having at least a first electrically conductive layer and a second electrically conductive layer disposed on a surface thereof; a first amount of a reagent composition that includes at least an effective amount of a hemoglobin sensitive redox mediator in contact with the first electrically conductive layer to define a working electrode and a second amount of a reagent composition in contact with the second electrically conductive layer to define a reference electrode; and a channel providing communication between the first amount and the second amount of reagent composition; wherein the sensor strip returns a measurable electrical signal indicative of the hemoglobin content of a blood sample having a volume in the range 1.6 micro liter to 10 micro liter in response to an application of voltage across the working electrode and the reference electrode when the blood sample is in contact with the first and second amount of reagent composition inside the channel.

According to another aspect of the present invention various methods may be employed to reliably determine the content of hemoglobin in a small blood sample (less than 2 micro liters) using a sensor strip according to the present invention. The methods may include linear scan voltammetry, amperometry, the combination of amperometry and impedance measurements as further detailed below.

A method according to the present invention for measuring the hemoglobin content of a sample of whole blood includes introducing a hemoglobin sensitive redox mediator into the blood sample; applying an initial electrical potential to the blood sample; increasing the electrical potential in discrete steps until reaching an end electrical potential; and measuring an electrical parameter of the whole blood after application of each electrical potential.

According to an aspect of the present invention the parameter can be a current value. The initial potential in one preferred embodiment may be −0.5 Volts, the end potential can be 0.3 Volts, and each discrete step may be 0.1 Volts per second.

According to another aspect of the present invention the impedance of the blood sample can be measured and the current values and the impedance values may be used together to obtain the hemoglobin content of the blood sample. Using the impedance values and the current values the hemoglobin content can be measured over an extended linear range. The extended linear range can be from at least 0 g/dL to 23 g/dL of hemoglobin.

The present application also discloses a method for measuring the hemoglobin content of a sample of whole blood that includes introducing a hemoglobin sensitive redox mediator into the sample of whole blood; obtaining an electrical current value for the sample of blood after the introducing step; obtaining an impedance value for the blood sample after the introducing step; multiplying the electrical current value with a first factor; multiplying the impedance value with a second factor; and adding the result of the first multiplication step to the result of the second multiplication; wherein the first factor and the second factor add up to one.

Advantageously, the volume of the blood sample can be as low as 1.6 µL. However, a sensor according to the present invention can perform accurately for blood samples of up to 10 µL.

The present invention also discloses a method for measuring hematocrit content in a sample of whole blood that includes measuring the hemoglobin content of the whole blood sample using a sensor strip that includes a base layer having at least a first electrically conductive layer and a second electrically conductive layer disposed on a surface thereof; a first amount of a reagent composition that includes at least an effective amount of a hemoglobin sensitive redox mediator in contact with the first electrically conductive layer to define a working electrode and a second amount of a reagent composition in contact with the second electrically conductive layer to define a reference electrode; and a channel providing communication between the first amount and the second amount of reagent composition; wherein the sensor strip returns a measurable electrical signal indicative of the hemoglobin content of a blood sample in response to an independent application of a variable voltage and a constant voltage across the working electrode and the reference electrode when the blood sample is in contact with the first and second amount of reagent composition inside the channel; determining the hematocrit content based on the measured hemoglobin content using a linear relationship of the form $$Hct = aHb + b$$

wherein Hct represents hematocrit content, Hb is the hemoglobin content and a and b are constants.

In one embodiment, the linear relationship may be determined by measuring the hematocrit content of the whole blood using another method; and correlating the results of the first measurement step with the second measurement step to obtain the linear relationship indicative of the hematocrit content in the whole blood.

According to another aspect of the present invention a sensor strip is configured for hemoglobin measurements in a whole blood sample and includes a base layer; at least a first electrically conductive layer, a second electrically conductive layer, and a third electrically conductive layer on the base layer; a first amount of a first reagent composition that includes at least an effective amount of a hemoglobin sensitive redox mediator in contact with the first electrically conductive layer to define a working electrode and a second amount of a second reagent composition in contact with the second electrically conductive layer to define a reference electrode; a third reagent composition in contact with the third conductive layer to define a blank electrode, the third reagent composition including a hemoglobin insensitive redox mediator; and a channel providing communication between the first amount and the second amount of the reagent composition; wherein the sensor strip returns a measurable electrical signal indicative of the hemoglobin content of a blood sample in response to an application of a voltage across the working electrode and the reference electrode when the blood sample is in contact with the first and second amount of the reagent composition inside the channel, wherein the measurable electrical signal is not influenced by the presence of an amount less than a maximum amount of an interfering oxidizable species, the maximum amount being determinable empirically by adding to a sample of whole blood different amounts of the interfering oxidizable species, measuring the current from the blank electrode and the working electrode after application of a voltage for each amount of added oxidizable species, determining a corrected current signal after each measurement of the current from the blank electrode and the working electrode based on a relationship having the form $$I = I2 - kI1$$

wherein I is the corrected signal proportional to hemoglobin content in the sample, I1 is the current value at the blank electrode, I2 is the current at the working electrode and k is a constant; and comparing each determined corrected signal to a respective reference value to determine whether the added interfering oxidizable species has influenced the measurable electrical signal.

The present application further discloses a method of measuring hemoglobin in whole blood using a sensor strip that includes a base layer; at least a first electrically conductive layer, a second electrically conductive layer, and a third electrically conductive layer on the base layer; a first amount of a reagent composition that includes at least an effective amount of a hemoglobin sensitive redox mediator in contact with the first electrically conductive layer to define a working electrode and a second amount of a second reagent composition in contact with the second electrically conductive layer to define a reference electrode; a third reagent composition in contact with the third conductive layer to define a blank electrode, the third reagent composition including a hemoglobin insensitive redox mediator; and a channel providing communication between the first amount and the second amount of the reagent composition; wherein the sensor strip returns a measurable electrical signal indicative of the hemoglobin content of a blood sample in response to an application of a voltage to the working electrode and the reference electrode when the blood sample is in contact with the first and second amount of the reagent composition inside the channel, the method including applying a first voltage across the blank electrode and the reference electrode for a first period of time; applying a second voltage across the working electrode and the reference electrode for a second period of time; and after an open circuit delay for a third period of time, applying linear scan voltammetry across the working and reference electrodes in voltage increments from an initial voltage value to a final voltage value at a predetermined rate to determine electrical current values at the voltage increments; and determining the hemoglobin content from the peak current value obtained from application of the linear scan voltammetry.

In one embodiment, the first voltage may be 0.7 Volts, the first period of time may be five seconds, the second voltage may be 1.0 Volt, the second period of time may be 10 seconds, the third period of time may be 17 seconds of open circuit followed by a linear potential scan, the initial voltage value may be −0.5 Volts, the final voltage value may be 0.3 Volts, and the predetermined rate may be 0.1 V/s.

The present application also discloses a method of measuring hemoglobin in whole blood using a sensor strip that includes a base layer; at least a first electrically conductive layer, a second electrically conductive layer, and a third electrically conductive layer on the base layer; a first amount of a reagent composition that includes at least an effective amount of a hemoglobin sensitive redox mediator in contact with the first electrically conductive layer to define a working electrode and a second amount of a second reagent composition in contact with the second electrically conductive layer to define a reference electrode; a third reagent composition in contact with the third conductive layer to define a blank electrode, the third reagent composition including a hemoglobin insensitive redox mediator; and a channel providing communication between the first amount and the second amount of the reagent composition; wherein the sensor strip returns a measurable electrical signal indicative of the hemoglobin content of a blood sample in response to an application of a voltage across the working electrode and the reference electrode when the blood sample is in contact with the first and second amount of the reagent composition inside the channel, the method including applying a first voltage across the blank electrode and the reference electrode for a first period of time; applying a second voltage across the working electrode and the reference electrode for a second period of time; and after an open circuit delay for a third period of time, applying a constant voltage while measuring the rise in current over time between the working and blank electrodes to determine the hemoglobin content.

In one embodiment the first voltage may be 0.7 Volts, the first period of time may be five seconds, the second voltage may be 1.0 Volts, the second period of time may be 10 seconds, and the third period of time may be 17 seconds while the circuit is open.

In the first embodiment of the present invention (FIGS. 1 and 2), the sensor of the present invention uses a 4-layer laminated construction, similar to the glucose sensor, which has been disclosed in U.S. Pat. Nos. 6,767,441; 6,287,451; 6,837,976, and U.S. patent applications Ser. Nos. 20060278537; 20070131549, the contents of which are incorporated herein by reference.

A practical configuration of a sensor according to the present invention may have a laminated, elongated body having a sample fluid channel connected between an opening on one end of the laminated body and a vent hole spaced from the opening. Within the fluid channel lie at least one working electrode and a reference electrode (or a counter electrode) in any order. The working electrode and the reference electrode are in electrical contact with respective conductive paths. The separate conductive paths terminate and are exposed for making an electrical connection to a reading device opposite the open channel end of the laminated body.

The laminated body may have a base insulating layer made from a plastic material, like polycarbonate, acrylics, polyesters, silicones, polyurethanes and the alike. At least two conductive paths may be delineated on the base insulating layer. The conductive paths may be deposited on the insulating layer by screen printing, by vapor deposition, or by any method that provides for a conductive layer that adheres to the base insulating layer. The conductive paths can be individually disposed on the insulating layer, or a conductive layer may be disposed on the insulating layer followed by etching/scribing the required number of conductive paths. The etching process may be accomplished by chemically, mechanically scribing lines in the conductive layer, using a laser to scribe the conductive layer into separate conductive paths, or by any other suitable method that will cause a break between and among the separate conductive paths required by the present invention. Conductive coatings or layers that may be used are coatings of nickel, gold, tin oxide/gold, palladium, other noble metals or their oxides, or carbon film compositions. The preferred conductive coatings are gold film or a tin oxide/gold film composition.

The laminated body may have a first middle insulating layer, also called a reagent holding/electrode area defining layer, on top of the base insulating layer and the conductive paths. The first middle layer, or reagent holding layer, includes at least two openings, one for receiving a working electrode and the other for receiving a reference electrode. Each opening corresponds to and exposes a small portion of an electrode surface. Preferably, the two openings in the middle layer have the same shape and dimensions, but have different shapes and/or dimensions without deviating from the scope and spirit of the present invention. The placement of all of the openings is such that they will be all positioned within the sample fluid channel described above. The first middle insulating layer is also made of an insulating dielectric material, preferably plastic, and may be made by die cutting the material mechanically, or with a laser, and then fastening the material to the base layer. An adhesive, such as a pressure-sensitive adhesive, may be used to secure the first middle insulating layer to the base layer. Adhesion may also be accomplished by ultrasonically bonding the first middle layer to the base layer. The first middle insulating layer may also be made by screen printing an insulating material or by binding a photopolymer over the base layer.

The laminated body may also have a second middle insulating layer, called a channel-forming layer, on top of the first middle layer. The second middle layer, or channel-forming layer, is also made of a plastic insulating material and creates the sample fluid channel of the laminated body. It contains a U-shaped cutout on one end which overlays the openings in the first middle layer with the open end corresponding to the open end of the laminated body described earlier. A double coated, pressure-sensitive adhesive tape may be used as the second middle layer.

The laminated body may also have a top layer with a vent opening and preferably an entrance notch. This layer is made of a plastic such as a polycarbonate, an acrylic, a polyester, a silicone, a polyurethane. The vent opening is located such that at least a portion of the vent opening overlays the bottom of the U-shaped cutout of the second middle insulating layer. The vent allows air within the sample fluid channel to escape as the sample fluid enters the sample entrance end of the laminated body. The notch is located at the sample entrance end. The sample fluid generally fills the sample fluid channel by capillary action. The extent of capillary action is dependent on the hydrophobic/hydrophilic nature of the surfaces in contact with the fluid undergoing capillary action. Capillary forces are enhanced by either using a hydrophilic insulating material to form the top layer, or by coating at least a portion of one side of a hydrophobic insulating material with a hydrophilic substance in the area of the top layer that faces the sample fluid channel between the sample entrance end of the laminated body and the vent opening of the top layer. It should be understood that an entire side of the top layer may be coated with the hydrophilic substance and then bonded to the second middle layer.

One opening may contain electrode material for the working electrode (W) loaded with hemoglobin sensitive chemicals and other ingredients, and one opening for the reference electrode (R). The positional arrangement of the working electrode and the reference electrode in the channel is not critical for obtaining usable results from the electrochemical sensor. The possible electrode arrangements within the sample fluid channel may be W-R or R-W, with the arrangement listed as the arrangement of electrodes would appear from the sample entrance end of the laminated body to the vent opening. The working electrode and the reference electrode are each in electric contact with separate conductive paths, respectively. The separate conductive paths terminate and are exposed for making an electric connection to a reading device on the end opposite the sample entrance end of the laminated body.

The working electrode may be loaded with a mixture of at least one compound capable of reacting with ferrous iron of hemoglobin, and optionally with one or more of a surfactant, a polymer binder, and a buffer. Preferably, the compound is an oxidant, more preferably, it is a redox mediator, whose reduced form is electrochemically active and detectable. The redox mediator can be selected from, but not limited to, various metal complexes and organic redox compounds. Examples of acceptable redox mediators are potassium ferricyanide, ferrocene and its derivatives, organometallic complexes of cobalt, osmium, rhodium, iridium and ruthenium, promazine, tetrathiafulvalene, methyl blue, 1,4-benzoquinone, 1,4-bis(N,N-dimethylamino) benzene, 4,4'-dihydrobiphenyl. The preferred mediator in the present invention is potassium ferricyanide. The reference electrode may be loaded with the same mixture as the working electrode. Preferably, the reference electrode opening is loaded with an oxidized form of redox mediator, such as potassium ferricyanide, along with other ingredients. The reference electrode opening could also be loaded with an Ag/AgCl layer (e.g., by applying Ag/AgCl ink or by sputter-coating silver or an Ag/AgCl layer) or other reference electrode materials.

When a liquid sample is applied to the sensor, the sample fills up the entire channel and covers both working electrode and reference electrode (or counter electrode). Electrochemical techniques including, but not limited to, cyclic voltammetry, linear scan voltmmetry, constant current potentiometry, constant potential amperometry, alternative current voltammetry, coulometry, and potentiometry are used to detect the electric signals generated from the working electrode. In the present invention, linear scan voltmmetry is preferred. Preferably, the potential scan starts from a relatively negative potential and ends at a relatively positive potential. The preferred starting potential is $-1.0$ V (vs. the reference electrode, if not stated otherwise). More preferably, the starting potential is $-0.5$ V. The preferred end potential is 1.2 V. More preferably, the end potential is 0.3 V. The scan rate (potential increment per second) may be from 1 mV/s to 10 V/s. Preferably, the scan rate is from 10 mV/s to 500 mV; more preferably, it is from 50 mV to 200 mV/s; still more preferably, it is around 100 mV/s. Thus, 8 s is needed to finish the potential scan from the starting potential $-0.5$ V to the end potential 0.3 V. The current signal at 0.2 V is measured, which is proportional to the hemoglobin concentration in the sample. The current results from the electro-oxidation of ferrocyanide (reduced form of ferricyanide) generated from the reaction between ferricyanide and ferrous iron of hemoglobin.

A pretreatment potential along with an open circuit delay may be applied before the potential scan. The pretreatment potential is used to oxidize the ferrocyanide resulting from the chemical matrix, thus, to reduce the background current. The preferred pretreatment potential is from 0.2 V to 1.2 V, more preferably; it is from 0.5 V to 1.0 V; still more preferably, it is around 1.0 V. The preferred time for the pretreatment is from is to 120 s, more preferably, it is from 5 s to 30 s; still more preferably, it is around 10 s. The open circuit delay allows the reaction between ferricyanide and ferrous iron of hemoglobin. The preferred time for the delay is from is to 180 s, more preferably, it is from 10 s to 60 s; still more preferably, it is around 17 s.

The impedance between the working electrode and the reference electrode can be measured at the beginning, or in the middle, or at the end of the pretreatment potential application. It is well known that impedance is related to the hematocrit or hemoglobin of a blood sample, i.e. higher hemoglobin concentration, higher impedance, or vice versa. As demonstrated below, a sensor according to the present invention allows accurate measurement of the impedance between the working electrode and the reference electrode. The impedance can be used to correct the current measurement to measure the hemoglobin content more accurately.

Disclosed below is a practical configuration of a second embodiment of the present invention which includes a similar structure and test procedure to the first embodiment, but it has one working electrode (W2), one reference electrode (R) and one blank electrode (W1). The working electrode and blank electrode may share the same reference electrode when potential is applied. A design according to the present invention also allows for the loading of different reagent mixtures and the application of different electrochemical techniques at the working and blank electrodes as desired. The working electrode is loaded with a hemoglobin sensitive material (e.g. potassium ferricyanide) and other ingredients; the blank electrode is loaded with a reagent optimized to respond to the oxidizable interferents. Various electrochemical techniques including, but not limited to, cyclic voltammetry, linear scan voltammetry, constant current potentiometry, constant potential amperometry, alternative current voltammetry, coulometry, and potentiometry can be used to detect the oxidizable interferents at the blank electrode. The "blank" electrode thus functions as an interference-indicative electrode. Such a three-electrode system not only possesses the feature of the first embodiment, but also the capability of eliminating interference from any oxidizable species coexisting with hemoglobin in blood samples, such as ascorbic acid, acetaminophen, uric acid, etc, by subtracting the background signals obtained at the blank electrode (W1) from the current signals obtained at the working electrode (W2).

The working electrode (W2) is loaded with a hemoglobin sensitive material (e.g. potassium ferricyanide) and other ingredients, while the blank electrode (W1) is loaded with a similar chemistry to the working electrode, but without adding a hemoglobin sensitive material, such that the "blank" electrode may function as an interference-indicative electrode. A proper potential and time and proper chemical composition are applied to the blank electrode so that the total concentration of oxidizable species can be measured accurately. The preferred potential is high enough to oxidize the oxidizable interferents, such as ascorbic acid, acetaminophen, uric acid and so on, but without oxidizing the electrode materials or electrolytes. The applied potential may be from about 0.2 V to about 1.2 V, more preferably from about 0.4 V to about 1.0 V, still more preferably about 0.7 V. The preferred time for the potential application is from about 1 s to about 30 s, more preferably, from about 2 s to about 10 s, still more preferably around 5 s. Note that the current signal represents the total concentration of the oxidizable species in the sample and thus the blank electrode functions as an interference-indicative sensor. By investigating the effect of the concentration of the oxidizable species on the current signal at the working electrode (W2), an accurate current signal, proportional to the hemoglobin concentration, can be obtained. It should be pointed that such a correction may not be simply subtraction or addition between the current signals at W1 and W2, because: 1) different electrochemical techniques may be applied to W1 (e.g. amperometry) and W2 (e.g. linear potential scan); 2) the time points to measure the current signals at W1 and W2 may be different; 3) the chemistries loaded at W1 and W2 may be different.

The working electrode is loaded with a hemoglobin sensitive material (e.g. potassium ferricyanide) and other ingredients, while the blank electrode is loaded with at least a compound capable of reacting with the oxidizable species in the sample, such that the "blank" electrode may also function as an interference-indicative electrode. The unique design of the present invention allows for loading different reagent compositions at the working and blank electrodes as desired. The reagent composition loaded at the blank electrode can be optimized to measure the oxidizable species other than ferrous iron of hemoglobin. The compounds can be selected from, but not limited to, various metal complexes and organic redox compounds. Examples of acceptable redox mediators are potassium ferricyanide, ferrocene and its derivatives, organometallic complexes of cobalt, osmium, rhodium, iridium and ruthenium, promazine, tetrathiafulvalene, methyl blue, 1,4-benzoquinone, 1,4-bis(N,N-dimethylamino) benzene, 4,4'-dihydrobiphenyl. The preferred mediator in the present invention is potassium ferricyanide. The preferred pH is around 7. The preferred electrochemical technique used for the blank electrode is amperometry. A proper potential and time are applied to the blank electrode so that the total concentration of oxidizable species can be measured amperometrically. The preferred potential may be from about 0.2 V to about 1.2 V, more preferably, from about 0.3 V to about 0.7 V, still more preferably about 0.4 V. The preferred time for the potential application is from about 1 s to about 30 s, more preferably from 2 s to 10 s, still more preferably about 5 s. Such a three-electrode system not only possesses the feature of the first embodiment, but also the capability of eliminating interference from any oxidizable species in the sample by correcting the current signals at the working electrode.

The operation of the blank electrode can be carried out before or after the operation of the working electrode, or at the same time as the working electrode. A design according to the present invention also allows for the application of different electrochemical detection techniques at the blank electrode without interfering with the operation at the working electrode.

The impedance between the working (or blank) electrode and the reference electrode can be measured at the beginning, or in the middle, or at the end of the above potential application. A design according to the present invention allows for the accurate measurement of the impedance between the blank electrode (W1) and the reference electrode (R), as well as between the working electrode (W2) and the reference electrode (R). The resulting impedance values can be used to correct the current measurement to obtain a more accurate hemoglobin measurement.

At least three conductive paths may be delineated on the base insulating layer. The first middle layer, or reagent holding layer, contains at least three openings for one working electrode, a reference electrode and one blank electrode. One opening contains electrode material for the working electrode (W2) loaded with a redox mediator and other ingredients; one for the blank electrode (W1) and one for the reference electrode (R). The positional arrangement of the working electrode, the reference electrode and the blank electrode in the channel is not critical for obtaining usable results from the electrochemical sensor. The preferred position was found to be W1-R-W2; that is, as the sample fluid entered the entrance open end of the laminated body, the fluid would cover W1 first, then R, then W2.

The working electrode and blank electrode may have separate reference electrodes (R1 and R2), one for the working electrode and the other one for the blank electrode, respectively. The positional arrangement of the working electrodes and the reference electrodes in the channel is not critical for obtaining usable results from the electrochemical sensor. There are numerous combinations for the positional arrangement. For example, one possible arrangement is W1-R1-W2-R2; that is, as the sample fluid enters the entrance open end of the laminated body, the fluid would cover W1 first, then R1, then W2, then R2.

A sensor according to the present invention may be devised without the first middle layer; i.e., the other three layers are the same as in the first embodiment. The detail of such a 3-layer layout has been disclosed in U.S. Pat. Nos. 6,258,229; 6,942,770, which are incorporated herein by reference. The U-shaped channel cutout is located at the sensor end (sample entrance end). The length, thickness and width of the U-shaped channel cutout define the capillary channel size or volume. The length and width of the U-shaped channel cutout, along with the base conductive layer, define the areas of the working and reference electrodes.

The working electrode (W) is loaded with at least a hemoglobin sensitive compound, and with one or more of a polymer binder, optionally one or more of a surfactant and one or more of a buffer. The reference electrode (R) may be covered by the same reagent mixture as the working electrode. Instead of the reagent mixture, the reference electrode could also be covered with a reference material, routinely used in the field, such as Ag/AgCl. This can be achieved by applying Ag/AgCl ink or by sputter-coating silver or an Ag/AgCl layer.

A sensor according to the present invention may have two channels (Channel 1 and Channel 2) on the same strip, arranged side by side, or back to back. At least one channel serves as the hemoglobin sensor having a similar structure to those mentioned in the above embodiments; at least one channel serves as the other sensor, e.g. interference indicative sensor. The sample entrance ends, or sampling entrances of the two channels, are close to each other; or the two channels simply share the same sampling entrance. In either case, the two channels are able to use the same drop of the blood sample. An example of a two channel construction can be found in U.S. Pat. No. 7,955,484, the contents of which are hereby incorporated by reference.

The number of the base conductive paths on the base insulating layer should match the total number of the electrodes in Channel 1 and Channel 2. There are two rows of openings on the second middle layer, one used for Channel 1 and the other one for Channel 2. Accordingly, the second middle layer has two U-shape cutouts, one used for Channel 1 and the other one for Channel 2. The laminated body also has a top layer with a vent opening for each channel. The two channels can also share one larger vent opening. Preferably each has an entrance notch at the sample entrance end. More preferably, the two channels share the same entrance notch, so that the two channels are able to use the same drop of the blood sample.

Channel 1 may have at least one working electrode and one reference electrode. At least one of the working electrodes is loaded with a hemoglobin sensitive material and other ingredients. Channel 1 can function independently as a hemoglobin sensor.

Channel 2 may have at least one working electrode and one reference electrode. At least one of the working electrodes is sensitive to the oxidizable species coexisting with hemoglobin in blood samples. Channel 2 can function independently as a sensor for the oxidizable species (interferences).

All of the advantages of the present invention will be made clearer upon review of the detailed description, drawings and appended claims.

BRIEF DESCRIPTION OF THE DRAWING(S)

DETAILED DESCRIPTION OF EMBODIMENTS OF THE INVENTION

The above mentioned embodiments of the present invention are illustrated in FIGS. 1-12.

Figure 1:
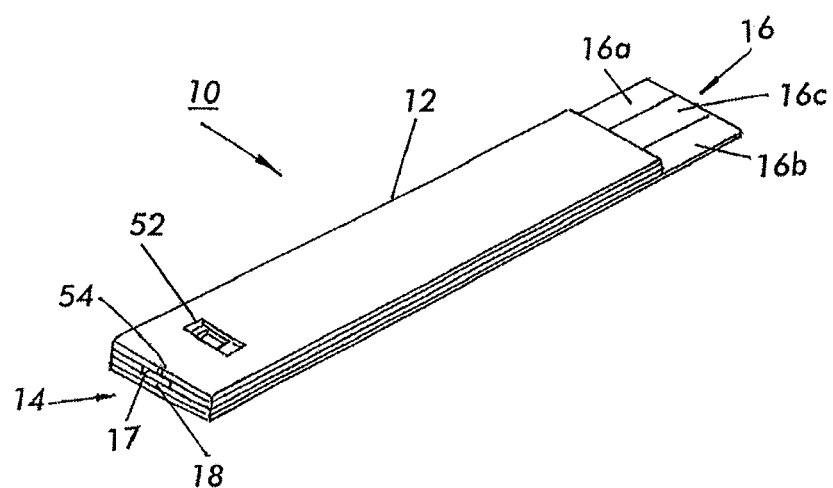
FIG. 1 is a perspective view of a test strip according to the first embodiment (two-electrode configuration) of the present invention.
Figure 2:
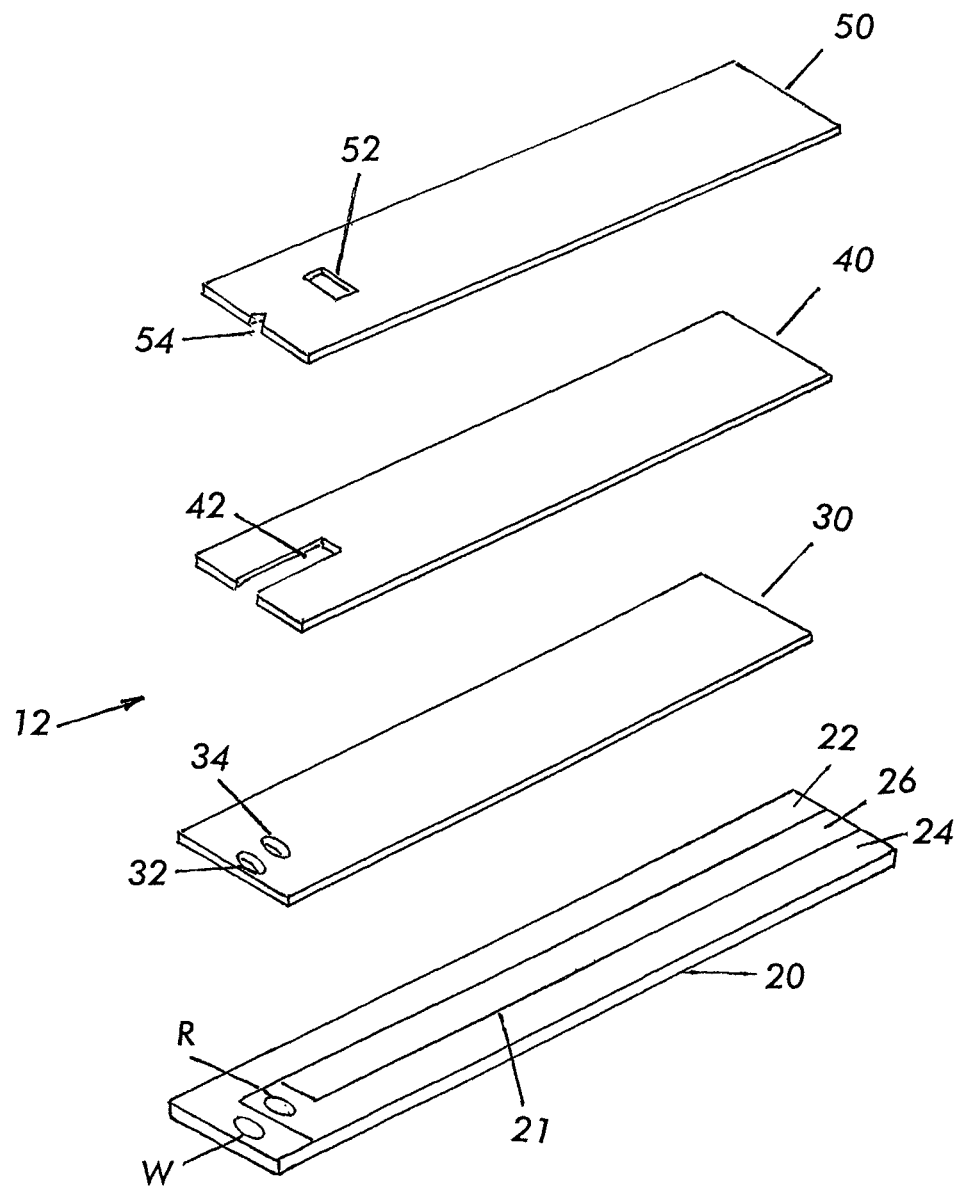
FIG. 2 is an exploded view of the first embodiment (two-electrode configuration) showing the four component layers of the test strip.
Figure 3:
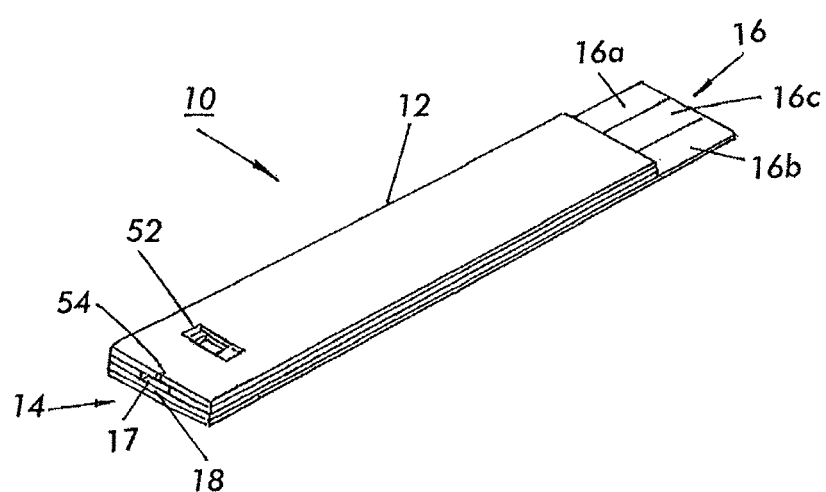
FIG. 3 is a perspective view of a test strip according to the second embodiment (three-electrode configuration) of the present invention.
Figure 4:
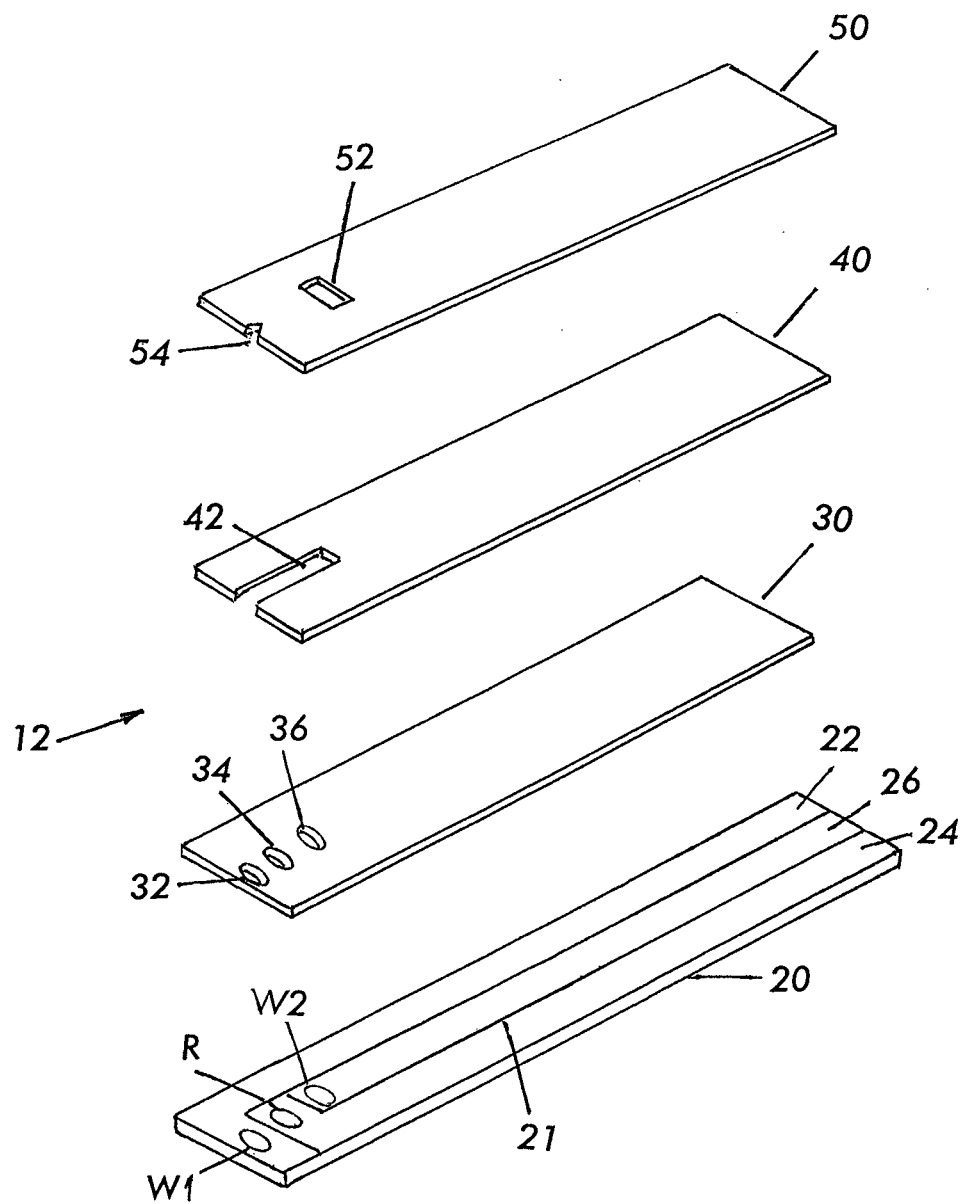
FIG. 4 is an exploded view of the second embodiment (three-electrode configuration) showing the four component layers of the test strip.

FIGS. 1 and 2 show a strip according to the first embodiment of the present invention (two-electrode configuration). FIGS. 3 and 4 show a strip according to the second embodiment of the present invention (three-electrode configuration). As will be understood from the disclosure below a strip according to the first embodiment of the present invention includes a working electrode and a reference electrode while the second embodiment includes a working electrode, a reference electrode and a blank electrode. Although one can devise hemoglobin sensor based on the two-electrode configuration (first embodiment) according to the principles disclosed herein, the three-electrode configuration (second embodiment), which possesses more features, will be described in detail below. The features of the second embodiment which employ the working electrode and the reference electrode can be equally applied to devise a strip according to the first embodiment of the present invention.

Unless indicated otherwise, all like numerals identify like features in the figures. Furthermore, "about" or "around" as used herein is intended to mean within a scientifically acceptable degree of error.

Referring to FIG. 3, sensor 10 has a laminated body 12, a fluid sampling end 14, an electrical contact end 16, and a vent opening 52. Sensor 10 may also include an optional inlet notch 54. Fluid sampling end 14 includes a sample chamber 17 between a sampling end inlet 18 and vent opening 52. Electrical contact end 16 has three discrete conductive contacts 16a, 16b and 16c.

Referring now to FIG. 4, laminated body 12 is composed of a base layer 20, a reagent holding layer 30, a channel forming layer 40, and a cover 50. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene and polystyrene.

Base layer 20 has a conductive layer 21 on which three spaced conductive paths 22, 24 and 26 are defined. Conductive paths 22, 24 and 26 may be formed by scribing or scoring conductive layer 21, or by silk-screening conductive paths 22, 24 and 26 onto base layer 20. Scribing or scoring of conductive layer 21 may be done by mechanically scribing the conductive layer 21 sufficiently to create at least three spaced and galvanically isolated conductive paths 22, 24 and 26. The preferred scribing or scoring method of the present invention is using a carbon dioxide laser, a YAG laser or an excimer laser. Conductive layer 21 may be made of any electrically conductive material such as, for example, gold, palladium, other noble metals or their oxides, or carbon film compositions. The preferred electrically conductive material is gold or other noble metals. A usable material for bottom layer 20 is a gold polyester film (Cat. No. FM-2) sold by Courtaulds Performance Films, Canoga Park, Calif. The gold polyester film was used in the construction of strips that were tested as described in detail below.

Reagent holding layer 30 has a first electrode opening 32 which exposes a portion of first conductive path 22, a second electrode opening 34 which exposes a portion of second conductive path 24, and a third electrode opening 36 which exposes a portion of third conductive path 26. Reagent holding layer 30 is made of a plastic material, preferably a medical grade, one-sided adhesive tape available from Adhesive Research, Inc., of Glen Rock, Pa. Acceptable thicknesses of the tape for use in the present invention are in the range of about 0.001 in. (0.025 mm) to about 0.01 in. (0.25 mm). One such tape, ARcareÒ 7815 (about 0.003 in. (0.075 mm)), is preferred due to its ease of handling and its ability to promote capillary action through the sample chamber of the sensor. It should be understood that the use of a tape is not required. Reagent holding layer 30 may be made from a plastic sheet and may be coated with a pressure sensitive adhesive, a photopolymer, ultrasonically-bonded to base layer 20, or silk-screened onto the base layer 20 to achieve the same results as using the polyester tape mentioned.

The electrode openings 32, 34 and 36 define electrode wells W1, R and W2, respectively, and hold chemical reagents forming a working electrode, a reference electrode, and a blank electrode. Generally, electrode well W2 is loaded with a hemoglobin sensitive reagent matrix that contains at least a redox mediator, a polymer binder, a buffer, and optionally, a surfactant. Electrode well W1 is loaded with a similar chemistry to W2, without adding the hemoglobin sensitive material. A reference matrix is loaded in electrode well R, it may be the same as the matrix for W1 or W2.

Typically, the reference matrix contains at least a redox reagent/couple or mediator such as, a reduced form of a redox mediator, an oxidized form of a redox mediator, or a mixture of a reduced and oxidized form of a redox mediator. If R is not loaded with a redox reagent/couple or mediator, working electrodes W2 and blank electrode W1 will not function properly. In the alternative, the reference electrode (electrode well R) may be loaded with a Ag/AgCl layer (e.g., by applying Ag/AgCl ink or by sputter-coating (a) a Ag layer followed by chloridizing the Ag or (b) a Ag/AgCl layer) or other reference electrode materials that do not require an additional redox mediator to function properly. Ag/AgCl is a type of redox couple, but it is not water-soluble. Therefore, if a reference electrode contains Ag/AgCl, an additional redox mediator may not be necessary.

The preferred shape of the reagent holding openings 32, 34, 36 is round and has a diameter of about 0.02 in to 0.04 in. The three reagent holding/electrode openings 32, 34 and 36 are adjacent each other and are spaced preferably about 0.005 in. to 0.1 in., preferably, it is about 0.045 in. (1.14 mm) from each other. The circular reagent holding openings are for illustrative purposes only. It should be understood that the shape and size of the reagent holding openings as well as the distance between the reagent holding openings are not critical, provided that the size of the openings is big enough to facilitate dispensing chemical reagents but small enough to allow for a reasonably small sample channel.

The positional arrangement of the working electrode, blank electrode and the reference electrode in the sample chamber is not critical for obtaining usable results from the hemoglobin sensor. The possible electrode arrangements within the sample chamber may be W1-B-W2, W1-R-W2, R-W1-W2, R-W2-W1, W2-R-W1, or W2-W1-R, with the arrangement listed as the arrangement of electrodes would appear from the sample inlet 18 of laminated body 12 to the vent opening 52. In the preferred embodiment, the relative positioning was found to be W1-R-W2. That is, as the fluid sample enters sampling end 14 of laminated body 12, the fluid sample would cover W1 first, then R, and then W2.

The working electrode, the blank electrode and the reference electrode are all in direct, galvanic contact with separate conductive paths. The separate conductive paths terminate and are exposed for making an electrical connection to a reading device on the end opposite the sample inlet 18 of laminated body 12.

Channel forming layer 40 has a U-shaped cutout 42 located at the fluid sampling end 14. The length of cutout 42 is such that when channel forming layer 40 is laminated to reagent holding layer 30, electrode areas W1, R and W2 are within the space defined by cutout 42. The length, width and thickness of the U-shaped cutout 42 define the capillary chamber volume. The thickness of channel forming layer 40 can affect the speed of the sample fluid flow into the sample chamber, which is filled by capillary action of the sample fluid. In the preferred embodiment, channel forming layer 40 can be made of a plastic material, a medical grade, double-sided pressure-sensitive adhesive tape available from Adhesive Research, Inc., of Glen Rock, Pa. Acceptable thicknesses of the tape for use in the present invention are in the range of about 0.001 in. (0.025 mm) to about 0.010 in. (0.25 mm). One such tape is ARcareÒ 7840 (about 0.0035 in. (0.089 mm)). U-shaped cutout 42 can be made with a laser or by die-cutting. The preferred method is to die-cut the cutout. The preferred size of the U-shaped cutout is about 0.215 in. long (5.46 mm), about 0.050 in. wide (1.27 mm), and about 0.0085 in. thick (0.216 mm). Thus, the channel volume in the preferred embodiment is around 1.6 µL.

Cover 50, which is laminated to channel forming layer 40, includes a vent opening 52 spaced from fluid sampling end 14 of hemoglobin sensor 10 to ensure that the sample in the sample chamber 17 will completely cover electrode areas W1, R and W2. Vent opening 52 is positioned in cover 50 so that it will align somewhat with U-shaped cutout 42. Preferably, vent opening 52 will expose a portion of and partially overlay the bottom of the U-shaped cutout 42. The preferable shape of vent opening 52 is a rectangle with dimensions of about 0.08 in. (2 mm) by about 0.035 in. (0.9 mm). The material for cover 50 may be a polyester film. In order to facilitate the capillary action, it is desirable for the polyester film to have a highly hydrophilic surface that faces the capillary chamber. Transparency films (Cat. No. PP2200 or PP2500) from 3M are the material used as the cover in the present invention. Cover 50 may optionally include inlet notch 54.

It should be understood that the conduit paths in any of the embodiments disclosed herein might be made from any non-corroding metal. Carbon deposits such as carbon paste or carbon ink may also be used as the conduit paths, all well known by those of ordinary skill in the art.

Redox Mediators

Although a lot of oxidants can oxidize ferrous iron of hemoglobin, an oxidized form of redox mediator is preferred, as the resulting reduced form of the redox mediator can be measured electrochemically. The redox mediators can be included at the working electrode W2, and, if included, an oxidized form of the redox mediators such as potassium ferricyanide is preferred. It is desirable that the mediator is stable in the matrix. It is still desirable that the mediator can maintain a desired potential for the hemoglobin working electrode. The mediator can be selected from, but not limited to, various metal complexes and organic redox compounds, such as potassium ferricyanide, ferrocene and its derivatives, organo-metallic complexes of cobalt, osmium, rhodium, iridium and ruthenium, promazine, tetrathiafulvalene, methyl blue, 1,4- benzoquinone, 1,4-bis(N,N-dimethylamino) benzene, and 4,4'-dihydrobiphenyl. The preferred mediator is an oxidized redox mediator, for example, potassium ferricyanide ($K_3Fe(CN)_6$).

In the preferred embodiment, the concentration of potassium ferricyanide in the reagent mixture is preferably 0.1% (W/W) to 20%. More preferably, the concentration of potassium ferricyanide is about 10%. If the concentration is below 0.1%, the sensor of the present invention may not give detectable and reproducible signal. If the concentration is above 20%, the sensor of the present invention may not give reproducible results. It should be noted that a silver or Ag/AgCl layer or other reference electrode materials can be applied to the reference electrode opening, which do not require the use of an additional redox mediator such as those listed above.

Polymer Binders

Polymers are used as binders to bind the ingredients on the electrode surfaces. They also serve as shields to protect the active compounds (e.g. the redox mediator) from moisture. Polymers should be sufficiently water-soluble and should also be capable of stabilizing and binding all other chemicals in the reagents in the electrode areas to the conductive surface layer. Preferably, at least two polymers can be added in the reagent mixture used in a strip according to the present invention. One of the preferred polymers is polyethylene oxide (PEO). Its molecular weight ranges from thousands to millions. Preferably, the molecular weight is over 1 million. More preferably, the molecular weight is about 4 million. Such a product is available from Scientific Polymer Products, NY, USA (MW 4,000,000, Cat No. 344). The concentration of PEO in the reagent mixture is preferably 0.04% (W/W) to 2%. More preferably, the concentration of PEO is about 0.6%. If the concentration is below 0.04%, the binding effect may not be strong enough to bind reagent to the electrode surface. As a result, the sensor of the present invention may not give accurate and reproducible results. If the concentration is above 2%, the reagent mixture would be too viscous to be dispensed precisely. As a result, the sensor of the present invention may not give reproducible results. The other polymer that can be used in the preferred embodiment is methylcellulose, which is available under the brand name of Methocel 60 HG (Cat. No. 64655, Fluka Chemicals, Milwaukee, Wis., USA). The concentration of Methocel 60 HG in the reagent mixture is preferably 0.02% (W/W) to 5%. More preferably, the concentration of Methocel 60 HG is about 0.5%. The reason for this range is similar to PEO.

Surfactants

Surfactants are used to facilitate dispensing of the reagent mixture into the openings for the working and reference electrodes, as well as for quickly dissolving the dry chemical reagents when a sample is applied to the channel. The surfactants, when selected properly, can facilitate the release of hemoglobin from a blood sample by lysing the blood sample. The amount and type of surfactants are selected to assure the previously mentioned functions. Surfactants can be selected from, but are not limited to, various anionic, cationic, nonionic and zwitterionic detergents, such as polyoxyethylene ether, Tween 20, sodium cholate hydrate, cholic acid, hexadecylpyridinium cholide monohydrate and CHAPs. The preferred surfactant is a polyoxyethylene ether. More preferably, it is t-octylphenoxypolyethoxyethanol and is available under the brand name Triton X-100. The concentration of Triton X-100 in the reagent mixture is preferably 0.01% (W/W) to 5%. More preferably, the concentration of Triton X-100 is about 1%. If the surfactant concentration is below or above the range, the sensor of the present invention may not give precise and accurate results. Optionally, an additional surfactant, such as cholic acid, may be added to the formulation to assure the previously mentioned functions.

The Buffer

A buffer may be present along with a redox mediator in dried form in a sensor strip according to the present invention. Examples of suitable buffers include citric acid, phosphates, carbonates, Tris and the like. Preferably, the pH of the buffer solution is above 7, more preferably, it is from 9 to 13, still more preferably, and it is around 12.5. If the pH is below 7, the interaction between ferrous iron of hemoglobin and the redox mediator (potassium ferricyanide) may not occur quickly (within one minute). Although at a pH above 13, the interaction still occurs, but the resulting sensor may not give accurate and precise results. Examples of buffers suitable for this pH include, but are not limited to, sodium or potassium salts of phosphates, carbonate, citrate, and acetate. Preferably, a combination of at least two sodium salts, like sodium phosphate and sodium carbonate, forming an alkaline buffer solution, is used to achieve the previously mentioned functions. More preferably, tri-sodium phosphate and sodium carbonate. The concentrations of the sodium salts in the reagent mixture are from 0.5% to 10% (W/W), preferably, about 1 to 3% (W/W). More preferably, the concentration of tri-sodium phosphate is 1.5% (W/W) and the concentration of sodium carbonate is 3% (W/W).

In the preferred embodiment, the reagent mixture (referred to below as "reagent mixture 1") used for the blank electrode (W1) contains 0.5% (W/W) Methocel 60 HG, 0.6% (W/W) polyethylene oxide, 1% (W/W) Triton X-100.

In the preferred embodiment, the reagent mixture (referred to below as "reagent mixture 2") used for the hemoglobin working electrode (W2) contains 0.5% (W/W) Methocel 60 HG, 0.6% (W/W) polyethylene oxide, 1% (W/W) Triton X-100, 1.5% tri-sodium phosphate dodecahydrate, 3% sodium carbonate and 10% potassium ferricyanide. In the preferred embodiment, reagent mixture 2 is also used for the reference electrode (R).

Preparation of the Reagent Mixtures

Reagent mixture 1 can be prepared as set forth below:

Into 100 ml of distilled water, add 0.5 g Methocel 60 HG, 0.6 g polyethylene oxide, and 1.0 g Triton X-100. Stir the solution until dissolved. The resulting solution is ready for dispensing.

Reagent mixture 2 can be prepared as set forth below:

Into 100 ml of distilled water, add 0.5 g Methocel 60 HG, 0.6 g polyethylene oxide, 10.0 g potassium ferricyanide, and 1.0 g Triton X-100, 1.5 g sodium tri-phosphate dodecahydrate, 3.0 g sodium carbonate. Stir the solution until dissolved. The resulting solution is ready for dispensing.

Sensor/Strip Construction

Assembly of the various embodiments of the present invention is relatively straightforward. Generally for the 4-layer configuration (illustrated in FIGS. 1-4), the base layer and reagent holding layer are laminated to each other followed by dispensing the reagent mixtures into their respective electrode wells. After drying the reagent mixtures, the channel forming layer is laminated onto the reagent holding layer and the cover is then laminated onto the channel forming layer. For other sensor constructions like side-by-side or back-to-back configurations, the base layer and the reagent holding layer are laminated to each other followed by dispensing the reagent mixtures within their respective electrode wells (or within each of the electrode wells in the legs of the side-by-side embodiment). After drying the reagent mixture, the channel forming layer is laminated onto the reagent holding layer and the cover is then laminated onto the channel forming layer.

More particularly, a piece of a gold polyester film is cut to shape as illustrated in FIG. 4, forming base layer 20 of sensor 10. A laser or the like (previously mentioned) may be used to score the gold polyester film. As also illustrated in FIG. 4, the film may be scored by the laser such that three electrodes at sample fluid end 14 and three contact points 22, 24 and 26 are defined at electrical contact end 16. The scoring line can be very thin but sufficient to create three separate, spaced, and galvanically isolated electrical paths. A scoring line 28 may optionally be made, but is not necessary, along the outer edge of base layer 20 to avoid potential static problems, which could cause a noisy signal from the finished sensor 10.

A piece of one-sided adhesive tape is then cut to size and shape, forming reagent holding layer 30 so that it will cover a major portion of conductive layer 21 of base layer 20 except for exposing a small electrical contact area as illustrated in FIG. 4.

Before attaching reagent holding layer 30 to base layer 20, three circular openings 32, 34 and 36 of substantially equal size are punched by laser, or by mechanical means such as a die-punch assembly, creating electrode openings 32, 34 and 36 in reagent holding layer 30. The preferred hole size for opening 32, 34 and 36 has a typical diameter of about 0.0276 in. (0.70 mm). As illustrated in FIG. 4, electrode openings 32, 34 and 36 are aligned with each other and have a spacing of about 0.045 in (1.14 mm) between them. The circular openings are for illustrative purposes only. It should be understood that the shape and size of the openings and the distance between the openings are not critical, provided that the size of the openings is big enough to hold sufficient chemical reagents for the electrodes to function properly but small enough to allow for a reasonably small sample chamber. As stated previously, the preferred arrangement of the electrodes formed in openings 32, 34 and 36 is W1 (blank electrode), R (reference electrode) and W2 (working electrode). Reagent holding layer 30 is then attached to base layer 20 in such a way as to define the electrode wells W1, R and W2.

The reagent mixture 1 is dispensed into electrode area W1. As described above, reagent mixture 1 is preferably a mixture of at least a polymer and a surfactant. Similarly, reagent mixture 2 is dispersed into electrode area R and W2. Reagent mixture 2 is preferably a mixture of a redox mediator (preferably potassium ferricyanide), at least a surfactant, a buffer and a polymer binder. Preferably, the reagents 1 and 2 are dispensed into W1, R and W2 at the same time and thus dried simultaneously at the same drying conditions. The volume dispensed into W1, W2 and R is from 40 to 110 nL for the sensor dimensions of the present invention. More preferably, it is from 50 to 90 nL, still more preferably, it is around 70 nL. If the volume is below 40 nL, the reagent mixture may not fully cover the electrode surface; if the volume is above 110 nL, the reagent mixture may over flow. Either way, the resulting sensor may not give accurate and precise results.

After the addition of the reagent mixtures, the reagent mixtures are dried. Drying of the reagents can occur within a temperature range of about room temperature to about 50° C. The length of time required to dry the reagents is dependent on the temperature at which the drying process is performed.

After drying, a piece of double-sided tape available from Adhesive Research is fashioned into chamber forming layer 40 containing U-shaped channel 42. Chamber-forming layer 40 is then layered onto reagent holding layer 30. As mentioned earlier, this chamber-forming layer 40 serves as a spacer and defines the size of the sample chamber 17. Its width and length are optimized to provide for a relatively quick moving fluid sample.

A piece of a transparency film (Cat. No. PP2200 or PP2500 available from 3M) is fashioned into top layer 50. A rectangular vent opening 52 is made using the laser previously mentioned or by means of a die-punch. Vent opening 52 is located approximately 0.212 in. (5.38 mm) from fluid entrance 54. Top layer 50 is aligned and layered onto chamber forming layer 40 to complete the assembly of sensor 10, as illustrated in FIG. 4.

Although the description of electrode construction above describes construction for a single sensor, the design and materials used are ideal for making multiple sensors from one piece of each layer material. This would be accomplished by starting with a relatively large piece of base layer having a conducting layer thereon. A plurality of scored lines are made into the conductive layer such that a repetitive pattern is created using the preferred scribing method previously described, whereby each pattern will eventually define the conductive paths for each sensor. Similarly, a large piece of the reagent holding layer material also having a plurality of openings in a repetitive pattern is sized to fit over the base layer in such a way that a plurality of sensors will be made when completed. The size of each aperture and the electrode material disposed in the plurality of electrode areas W1, R and W2 are similar to that disclosed above. After disposing the reagent mixture in their respective reagent holding openings and drying, a large piece of the channel forming layer material having a plurality of elongated apertures is layered onto the reagent holding layer material such that each elongated aperture of the channel forming layer material contains corresponding openings of the reagent holding layer material. A comparably-sized cover layer material having a plurality of vent openings and notch-forming openings in a repetitive pattern is layered onto the chamber forming layer material. The laminated sheet is then cut in appropriate locations to form individual sensor strips.

Sensor/Strip Application

A hemoglobin strip according to the second embodiment of the present invention can be used along with a hand-held meter to determine the content of hemoglobin in a small sample (less than 2 micro liters) of whole blood. The strip may be inserted into the strip connector and thus the meter is triggered. About 1.6 µL of blood is applied to the hemoglobin strip. Once a blood sample enters the capillary channel of the hemoglobin strip of the present invention, a potential of approximately 0.7 Volt is applied across the blank electrode (W1) and the reference electrode (R) and the resultant current signals are recorded against time (amperometry). The current at 5 seconds time is proportional to the oxidizable species (interferents) coexisting with hemoglobin in the sample, thus it is used to correct the current signal obtained at the working electrode (W2).

After the amperometric measurement at the blank electrode (W1), a potential of 1.0 Volt is applied to the working electrode (W2) for about 10 s in order to convert (oxidize) the reduced form of the mediator (Fe(II)) to its oxidized form (Fe(III)), thereby minimizing the background noise and improving the performance of the sensor. After an open circuit delay (e.g. about 17 seconds) to allow Fe(III) to react with hemoglobin iron (HbFe(II)), a linear potential scan is carried out. In the preferred embodiment, the starting scan potential is around −0.5 Volt and end potential is around 0.3 Volt. The scan rate is around 0.1 V/s. The time for the scan is about 8 s. The current response at a fixed potential (e.g. 0.2 Volt) or peak current (around 0.2V) is proportional to the hemoglobin concentration. The total time for the test is around 40 s (5+10+17+8 s). The hemoglobin strip of the present invention is designed for single use meaning that it cannot be reused after one application and will be discarded after use.

The following methods illustrate the efficacy of a sensor strip according to the present invention. All sensors of the present invention were tested on a hand-held hemoglobin meter manufactured by Nova Biomedical Corporation of Waltham, Mass. In order to obtain the reference values, the same samples might also be tested with a reference analyzer, like HemoCue system (HemoCue Inc., Cypress, Calif.), Sysmex Hemotology system (Kobe, Japan). The sensors used in the methods disclosed below were devise according to the preferred reagent compositions and preferred materials disclosed above.

Voltage Scan (Variable Voltage) and Amperometry (Constant Voltage) Methods

To obtain optimum electrochemical detection techniques, several electrochemical techniques were pursued including cyclic voltammetry, linear scan voltammetry, amperometry, coulometry, potentiometry, chronopotentiometry and so on. The preferred methods were determined to be linear scan voltammetry and amperometry.

The procedure for the linear scan voltammetry was carried as below: first, a potential of approximately 0.7 Volt was applied to the blank electrode (W1) for 5 s; second, a potential of 1.0 Volt was applied to the working electrode (W2) for 10 s; third, after an open circuit delay (17 s), and a linear scan voltammetry was conducted with an initial potential of −0.5 Volt and end potential of 0.3 Volt and scan rate of 0.1 V/s.

Figure 5:
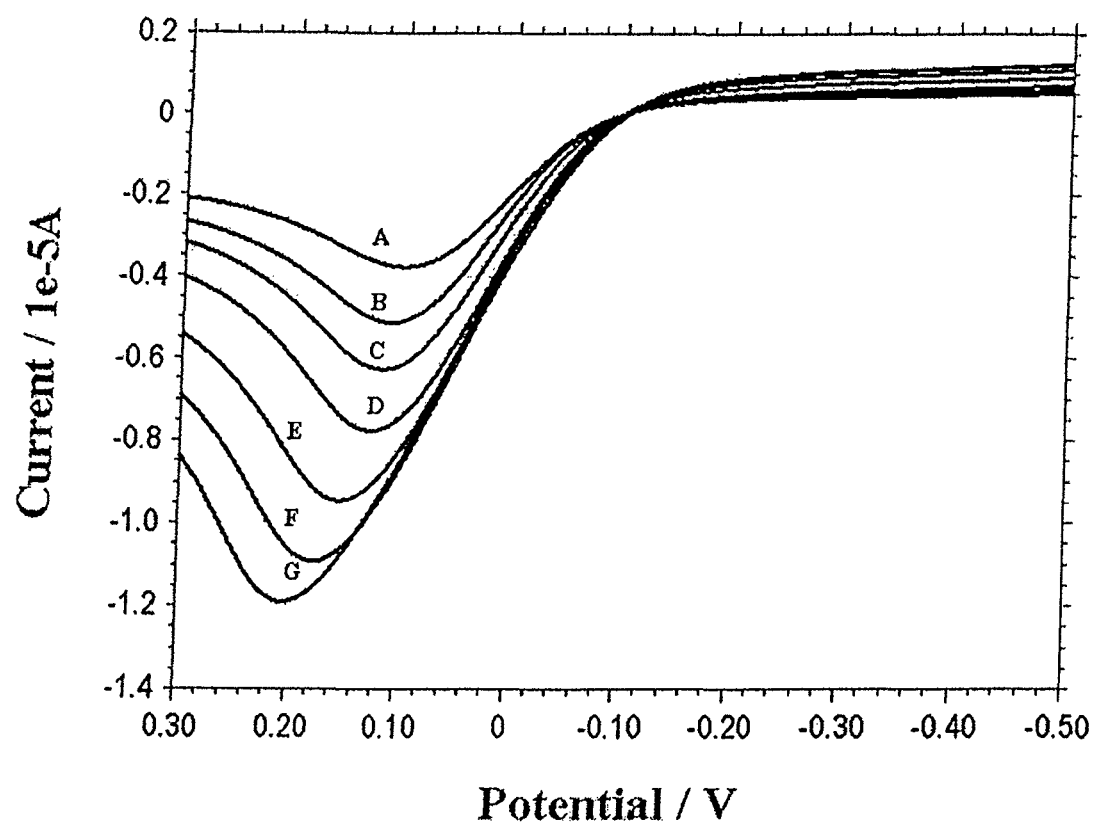
FIG. 5 shows linear scan voltammograms of a blood samples using strips according to the present invention.

FIG. 5 shows the linear scan voltammograms for the blood samples of different levels of hemoglobin using the hemoglobin strips of the present invention. The electro-oxidation peak at around 0.1 to 0.2 Volt (A to G) is attributed to the re-oxidation of ferrocyanide generated from electro-reduction and the interaction between ferricyanide and ferrous iron of hemoglobin in the blood samples (see Table 1 below). FIG. 5 shows that the peak currents or the current values at a fixed potential (e.g. 0.2 Volt) increase linearly with increasing the hemoglobin concentration (A to G). The hemoglobin values were obtained with HemoCue System (HemoCue Inc., Cypress, Calif.).

TABLE 1

| Sample | Hemoglobin Concentration (g/dL) |
|---|---|
| A | 0 |
| B | 5.1 |
| C | 7.0 |
| D | 9.6 |
| E | 13.5 |
| F | 17.0 |
| G | 19.5 |

Figure 6:
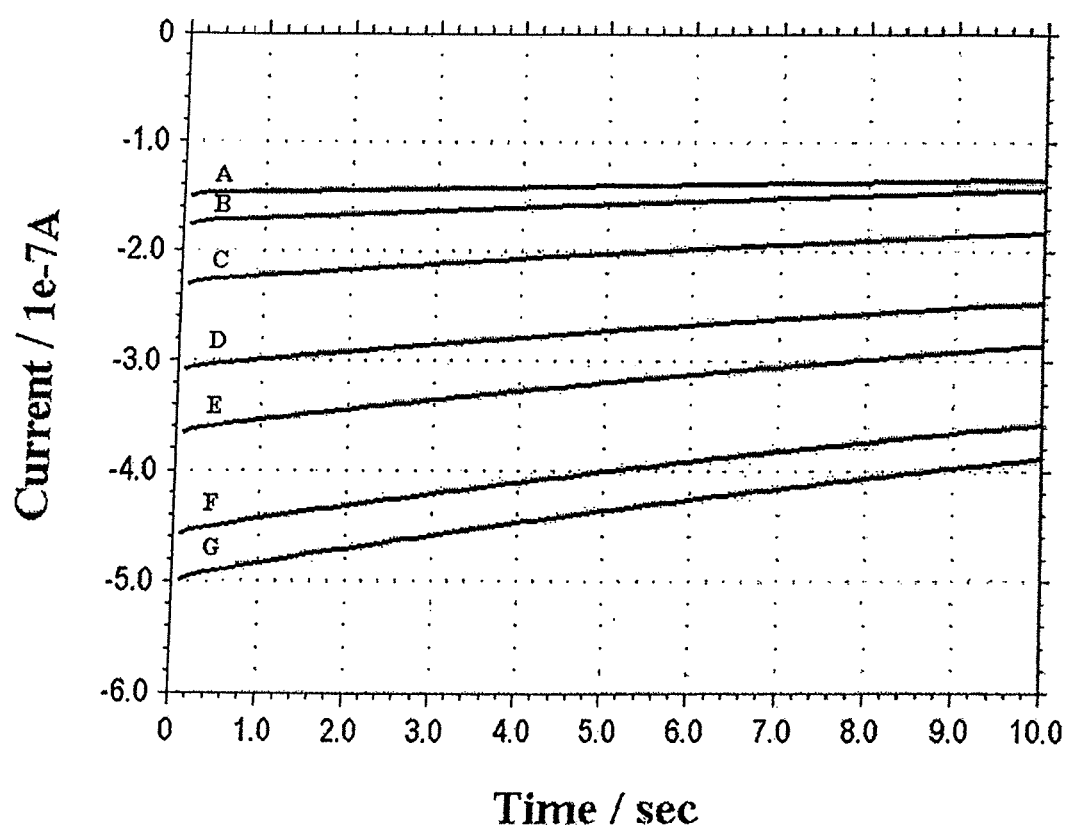
FIG. 6 shows amperometric i-t curves of the blood samples using strips according to the present invention.

The amperometry was conducted using the following procedure: first, a potential of approximately 0.7 Volt was applied to the blank electrode for 5 s; second, a potential of 1.0 Volt was applied to the working electrode for 10 s; third, after an open circuit delay (17 s), the constant potential of 0.2 Volt was applied and the currents vs. time curves were recorded. FIG. 6 shows the amperometric i-t curves for the same blood samples A-G as in FIG. 5 (see Table 1). FIG. 6 shows that the currents at a given time point increase with increasing the hemoglobin concentration (A to G), but the linearity is not as good as that obtained from linear scan voltammetry.

Voltammetry and Impedance Measurements Combined

Figure 7:
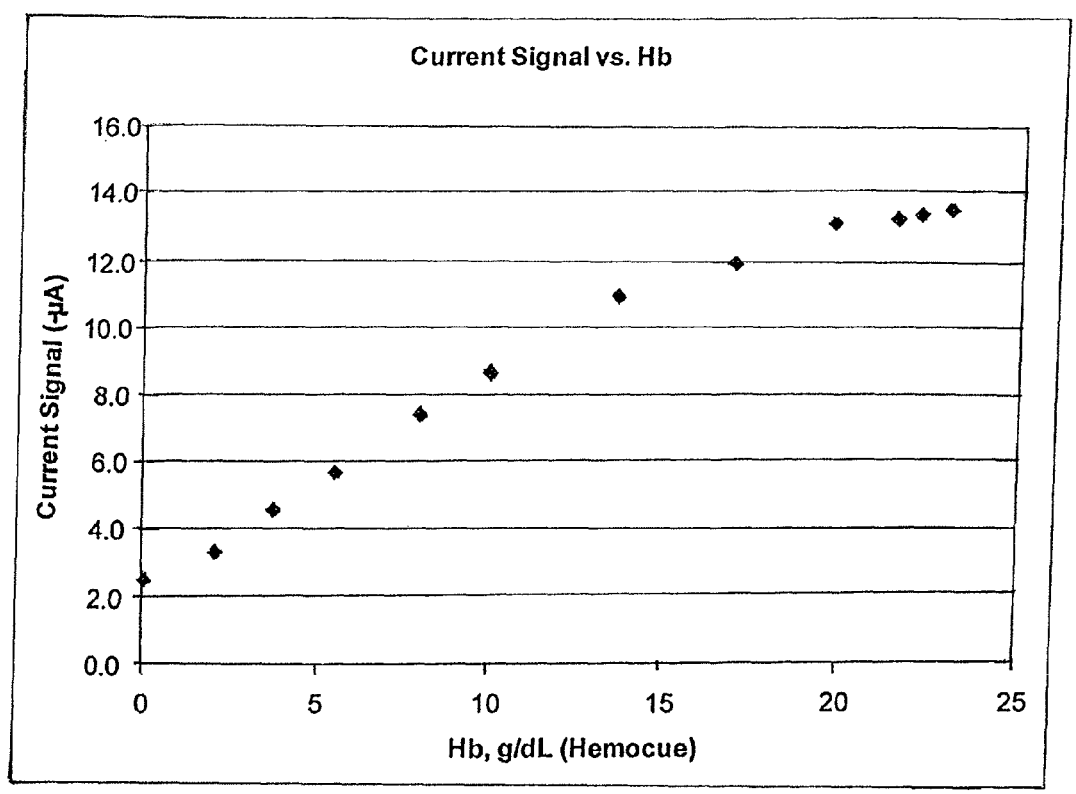
FIG. 7 shows the dependence of the current signal obtained with linear scan voltammetry on the hemoglobin concentration.

A sample of venous blood was collected in a heparinized green top tube and spun to separate plasma and red cell. The red cell and plasma were recombined to make blood samples with different levels of hemoglobin. Each sample was measured with the HemoCue system and then with sensors of the present invention along with the hand-held hemoglobin meter. About 1.6 μL of blood is applied to the hemoglobin strip, the test result is displayed in about 40 s on the meter FIG. 7 depicts the dependence of current signals obtained with linear scan voltammetry on the concentration of hemoglobin obtained using the reference analyzer (HemoCue meter). It should be noted that the current response is linear from 0 to about 20 g/dL hemoglobin, then it starts to level off above that range.

Figure 8:
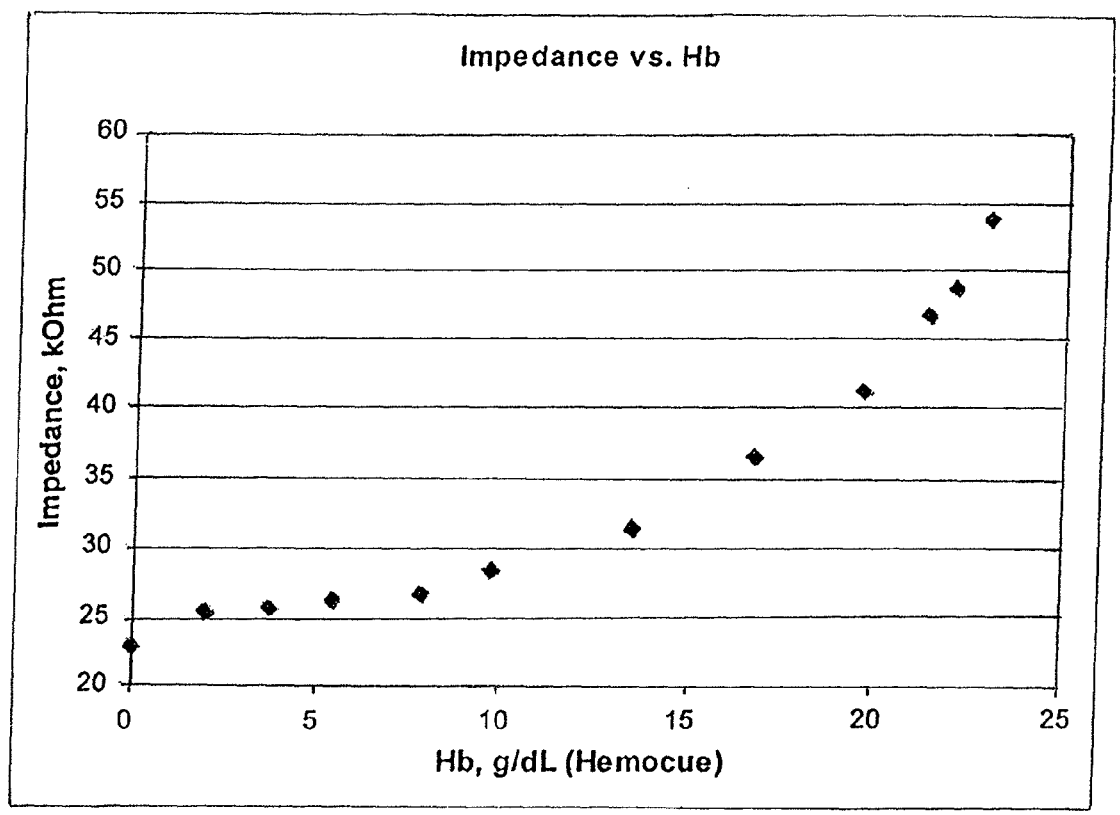
FIG. 8 shows the dependence of the impedance on the hemoglobin concentration.

FIG. 8 shows the dependence of impedance on the concentration of hemoglobin obtained using the reference analyzer (HemoCue meter). The impedance increases slightly with increasing the hemoglobin concentration below around 7.8 g/dL, while it shows excellent sensitivity above that. Thus, a combination of the use of the current signal values and impedance values could make the hemoglobin measurement more accurate and make the linear range broader.

Hemoglobin concentration (Hb) can be calculated from the following equations:

$$Hb = aHb(i) + bHb(Imp) \qquad (1)$$

$$a + b = 1 \qquad (2)$$

Where Hb is hemoglobin (g/dL);
Hb(i) is hemoglobin value based on the current signal;
Hb(Imp) is hemoglobin value based on the impedance;
a and b are coefficients equaling 0 to 1.

Figure 9:
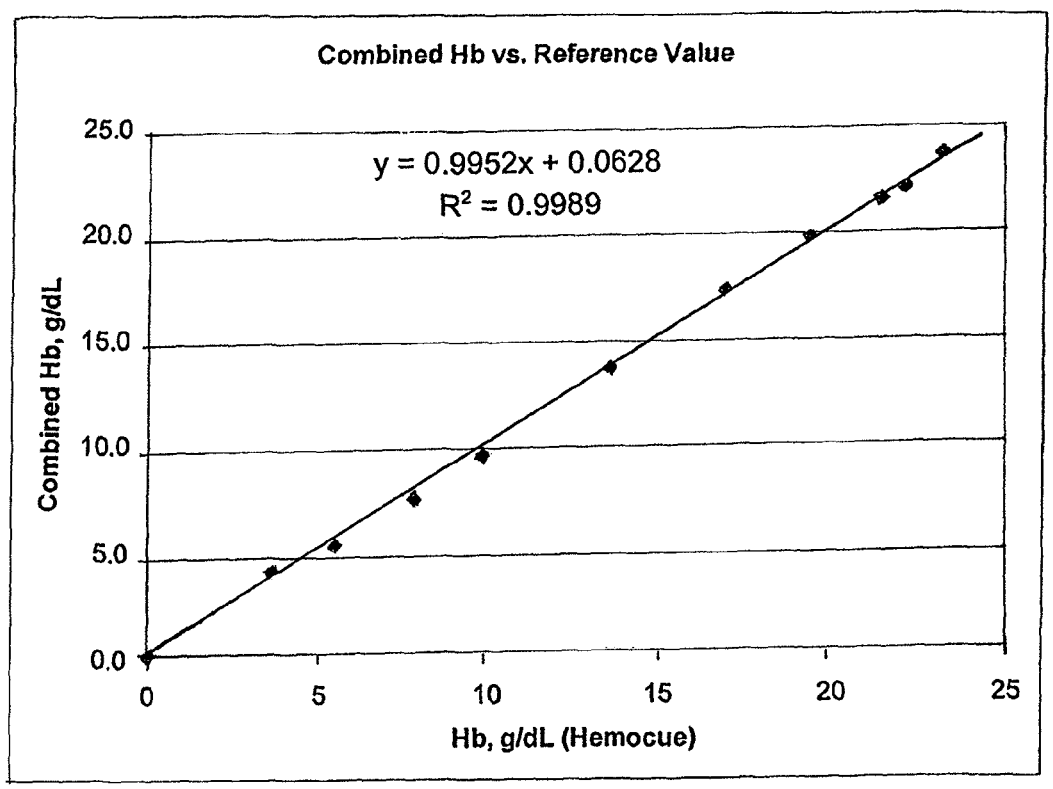
FIG. 9 shows the combined Hb (aHb(i)+bHb(Imp)) results vs. reference value(HemoCue), which indicates the extended linear range of strips according to the present invention.

In order to demonstrate the advantage of the use of both current signals and impedance values, the combined hemoglobin concentration readings (Hb), which combine Hb(i) and Hb(Imp) using the equations (1) and (2), were plotted against the concentration values obtained using the reference analyzer (HemoCue meter) and are illustrated in FIG. 9. It is obvious that the combined results are superior to Hb(i) or Hb(Imp) alone. As a result, the sensors of the present invention show an extended linear range up to 23 g/dL.

The precision of the sensors of the present invention was investigated by testing the same sample multiple times. Three different batches of sensors of the present invention were used and three hemoglobin levels of the blood samples were tested for this purpose. Typically, the coefficient of variation (CV %) was about 4.0, 3.6 and 3.8% for samples containing 7.5, 14.0 and 20.0 g/dL levels of hemoglobin (n=20), respectively.

Elimination of the Influence of Interferents

The unique design of the three-electrode system of the second embodiment of the present invention makes it possible to eliminate the interference from co-existing species that are oxidizable at the electrode. This is achieved by measuring the total concentration of the oxidizable species at the blank electrode (W1) and correcting the current signals at the working electrode (W2). The correction is represented by the following equation:

$$I = I_2 - kI_1 \qquad (3)$$

Where $I_2$ is the current at W2 (working electrode);
$I_1$ is the current at W1 (blank electrode);
k is a constant related to the electrode areas, capillary channel structure and other factors;
I is the corrected current signal which is proportional to the hemoglobin concentration in the sample.

To evaluate the interference effect, blood samples were spiked with different concentrations of interferents. The samples were then tested with the hemoglobin strips according to the second embodiment of the present invention. The blood samples were also tested with HemoCue system (HemoCue Inc., Cypress, Calif.) for the reference values. The test results showed that, up to 10 mg/dL acetaminophen, ascorbic acid, hydroxyurea, 15 mg/dL bilirubin, 8 mg/dL tolazamide, 30 mg/dL salicylic acid, 20 mg/dL uric acid, have no influence on the determination of hemoglobin concentration using hemoglobin strips according to the second embodiment of the present invention. The maximum value for each interferent cited above represents the maximum concentration of the interferent which may co-exist in the blood sample. Each maximum value is significantly above an upper limit that would be of clinical importance. Thus, the test indicates that the performance of a sensor according to the present invention does not suffer because of the presence of the above mentioned interferents even in significant amounts.

Other common interference is from electrolytes, such as sodium chloride, which varies from sample to sample and could be a major issue for other type of hemoglobin sensors (e.g. impedance or conductivity based sensors). In order to evaluate the effect of varying concentrations of the electrolytes on the hemoglobin measurement using the sensors of the present invention, a blood sample was spiked with different levels of sodium chloride. The test results showed that up to 30 mM of NaCl spiked to the blood samples has no substantial effect on the hemoglobin measurement. The maximum value of NaCl mentioned above is the maximum, tolerable NaCl concentration that may exist in a blood sample. This maximum value is significantly above an upper limit of clinical importance. Thus, the test indicates that the performance of a sensor according to the present invention does not suffer because of the presence of NaCl even in significant amounts.

Figure 10:
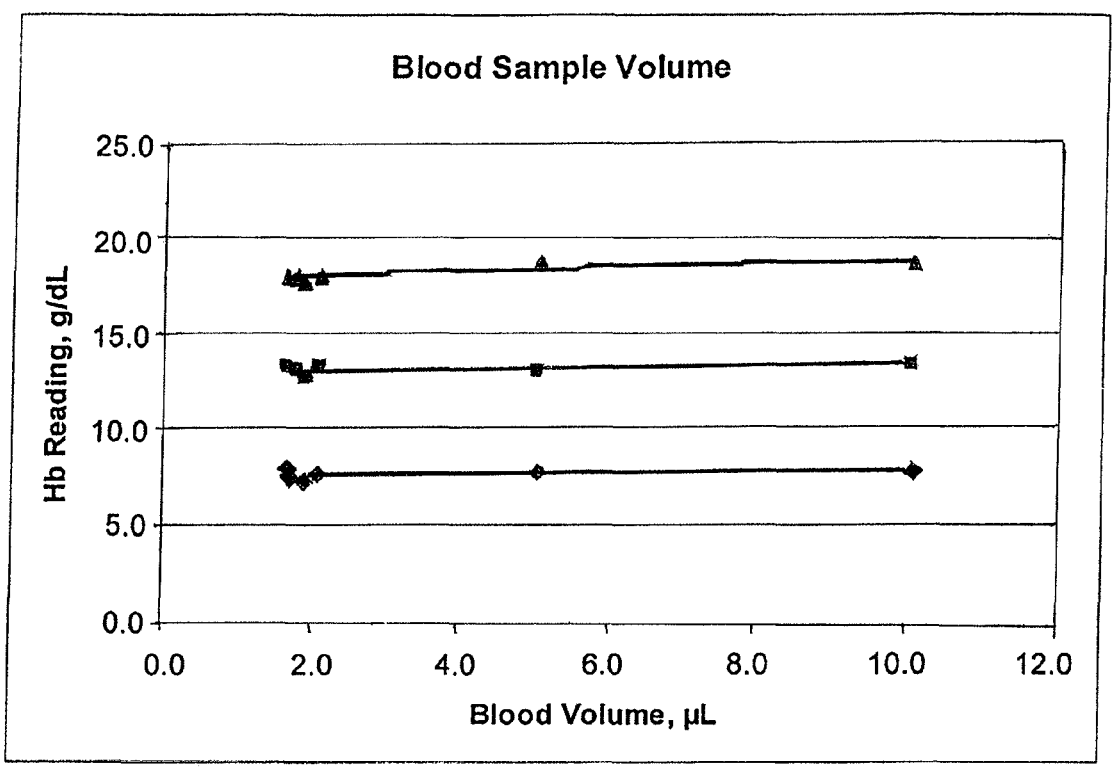
FIG. 10 illustrates the ability of strips according to the present invention to provide reliable measurements of the hemoglobin content in a small sample of whole blood (less than 2 micro liters).

Accuracy of Results for Samples Having a Volume in the Range 1.6-10 Micro Liters Advantageously, a method according to the present invention employing a strip according to the second embodiment of the present invention requires very little blood to produce accurate results. Blood volume required for the measurement of hemoglobin is determined by the capillary channel volume. The calculated volume for the capillary channel of the present invention is about 1.6 µL. In order to test the volume effect on the sensor response, different blood sample volumes (1.6 to 10.0 µL) were applied to the sensors. It should be pointed that excessive blood (>1.6 µL) would not enter the capillary channel as the channel can hold only up to 1.6 µL. The test data are displayed in FIG. 10. Obviously, the sensors of the present invention show no dependence of the response on the sample volume from 1.6 to 10 µL. Thus, the minimum volume required to obtain precise results is 1.6 µL. FIG. 10 illustrates that as little as 1.6 µL of blood can be used to produce accurate results when employing the inventive concepts described herein.

Figure 11:
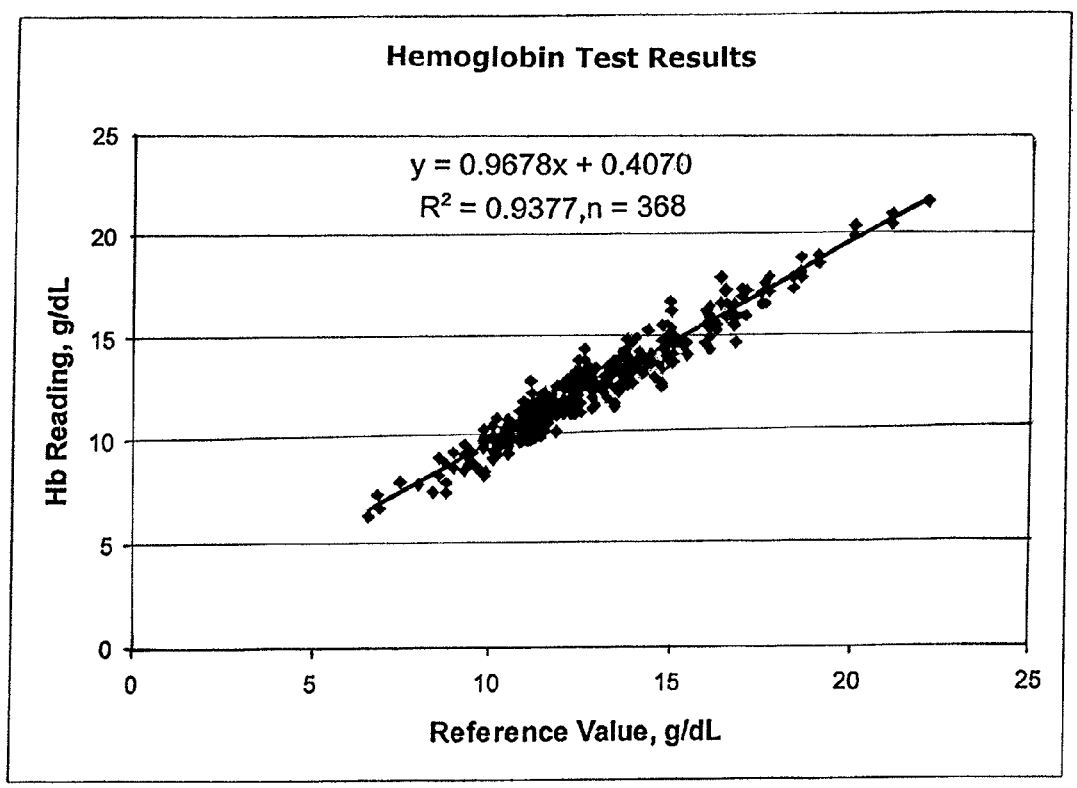
FIG. 11 shows the determination of hemoglobin using the hemoglobin sensors according to the present invention to varying hemoglobin in the blood samples.

Demonstration of Accuracy of Hemoglobin Measurements Using Sensors According to the Present Invention Sensor strips according to the present invention may be used along with a hand-held hemoglobin meter. Heparinized blood samples (green top) with different hemoglobin concentrations (un-synthetic) were tested with the hemoglobin sensors of the present invention. The same samples were also tested with a reference method (Sysmex Hemotology System, Kobe, Japan). About 2 µL of blood were applied to the hemoglobin strip. The test result were obtained in about 39 s by the meter. FIG. 11 summarizes the test results for a total of 184 samples and 368 data points (each sample has a duplicate result). As seen from the graph, the sensors of the present invention respond to the hemoglobin concentration in the blood samples over a tested range of about 6.6 g/dL to about 22.0 g/dL. A regression equation of y=0.9678x+0.4074, R square of 0.9377 and total number of 368 were obtained.

Determination of Hematocrit Using Sensor Strips According to the Present Invention Hematocrit is a measurement of the fractional volume of red blood cells. To measure hematocrit using hemoglobin sensor strips according to the present invention, a correlation between hematocrit and hemoglobin was established by measuring the hemoglobin content of blood samples with the hemoglobin strips of the present invention and with a microcentrifuge (the reference method recommended by NCCLS of determining hematocrit or packed cell volume (PCV) is centrifugation.) The correlation between hematocrit and hemoglobin was found to be:

$$Hct = aHb + b \qquad (4)$$

Where Hct represents hematocrit (%);
Hb represents hemoglobin (g/dL);
a and b are empirical constants, which equal to 2.805 and 2.205 respectively, under the present conditions, respectively.

Figure 12:
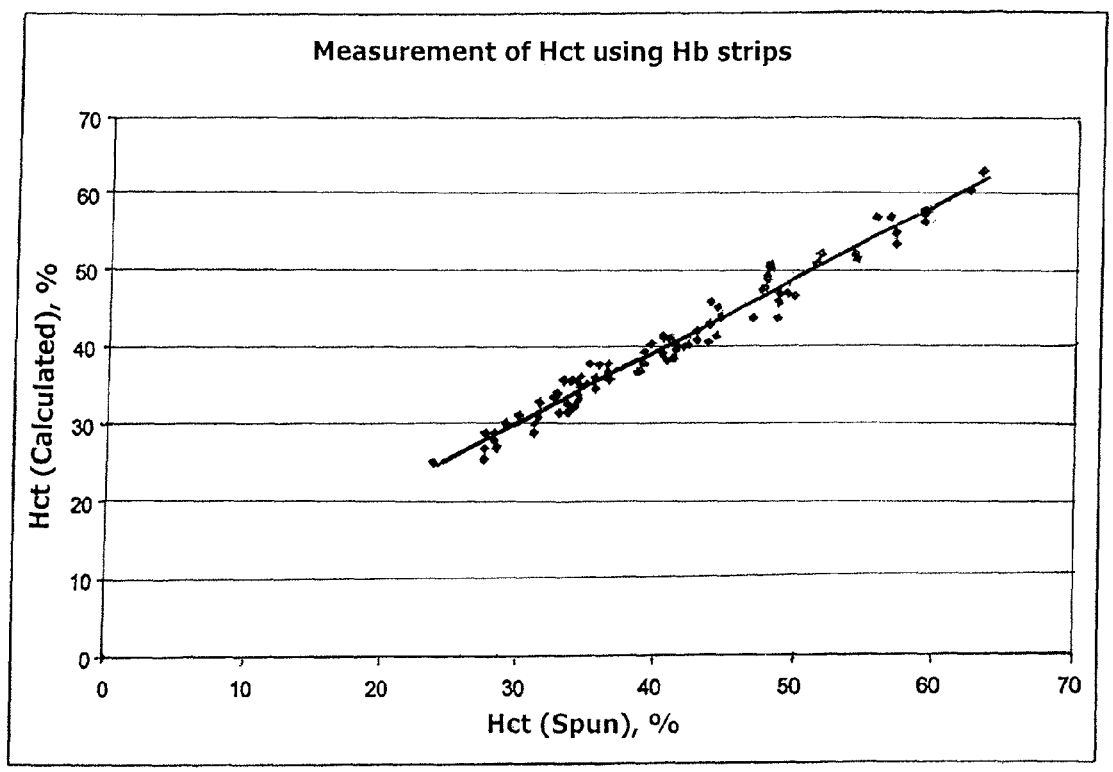
FIG. 12 shows the measurement of hematocrit using strips according to the present invention.

Therefore, once hemoglobin concentration is measured, Hct can be easily calculated using the above equation (4). FIG. 12 shows the hematocrit test results using the hemoglobin strips of the present invention.

Note that although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A sensor strip configured for hemoglobin measurements in a whole blood sample, comprising:
   a base layer having at least a first electrically conductive layer and a second electrically conductive layer disposed on a surface thereof;
   a first amount of a reagent composition that includes at least an effective amount of a hemoglobin sensitive redox mediator and an effective amount of polymer binder in contact with said first electrically conductive layer to define a working electrode and a second amount of a reagent composition that includes an effective amount of polymer binder in contact with said second electrically conductive layer to define a reference electrode; and
   a channel providing communication between said first amount and said second amount of reagent composition;
   wherein said sensor strip returns a measurable electrical signal indicative of the hemoglobin content of a blood sample in response to an independent application of a variable voltage and a constant voltage across said working electrode and said reference electrode when said blood sample is in contact with said first and second amounts of reagent composition inside said channel.

2. The sensor strip of claim 1, wherein said redox mediator oxidizes hemoglobin iron (II).

3. The sensor strip of claim 1, wherein said redox mediator comprises potassium ferricyanide.

4. The sensor strip of claim 3, wherein said redox mediator is in the range 0.1% to 20% (W/W) of said reagent composition.

5. The sensor strip of claim 4, wherein said reagent composition further comprises an effective amount of surfactant and at least one buffer.

6. The sensor strip of claim 5, wherein said polymer binder is in the range 0.04% to 2% (W/W) of said composition, said surfactant is in the range 0.01% to 5% (W/W) of said composition and said buffer has a pH above 7.

7. The sensor strip of claim 6, wherein said polymer binder comprises polyethylene oxide, said surfactant comprises a polyoxyethylene ether and said buffer comprises an alkaline composition.

8. The sensor strip of claim 1, further comprising a first middle layer over said base layer, a second middle layer over said first middle layer and a top layer, said first middle layer including a first opening that registers with said first conductive layer in which said reagent composition is received and a second opening that registers with said second conductive layer in which said reagent composition is received, said second middle layer including a cut away residing above said first and said second openings to define said channel, and said top layer including a vent opening in communication with said channel, wherein said channel is sized to receive no more than 2 micro liters of whole blood.

9. The sensor strip of claim 1, further comprising a third electrically conductive layer on said base layer and a third reagent composition in contact with said third conductive layer to define a blank electrode, said third reagent composition including a hemoglobin insensitive redox mediator.

10. The sensor strip of claim 9, further comprising a first middle layer over said base layer, a second middle layer over said first middle layer and a top layer, said first middle layer including a first through opening that registers with said first conductive layer in which said reagent composition is received, a second through opening that registers with said second conductive layer in which said reagent composition is received and a third opening that registers with said third conductive layer in which said second reagent composition is received, said second middle layer including a cut away residing above said first, said second and said third openings to define said channel, and said top layer including a vent opening in communication with said channel, wherein said channel is sized to receive no more than 2 micro liters of whole blood.

11. The sensor strip of claim 1, wherein said reagent composition in contact with said second electrically conductive layer comprises an Ag/AgCl stack instead of said redox mediator.

12. The sensor strip of claim 1, wherein said blood sample has a volume in the range of 1.6 micro liter to 10 micro liter.

13. The sensor strip of claim 1, wherein said first amount of said first reagent composition and said second amount of said second reagent composition are identical compositions.

14. A method for measuring hemoglobin in whole blood with a sensor strip according to claim 1 that contains a blood sample in contact with the first and the second amounts of reagent composition, said method comprising:
applying linear scan voltammetry and measuring current passing through said blood sample.

15. A method for measuring hemoglobin in whole blood with a sensor strip according to claim 1 that contains a blood sample in contact with the first and the second amounts of reagent composition, said method comprising:
obtaining current values by linear scan voltammetry and impedance values for said blood sample, and obtaining the hemoglobin content of said blood sample based on said current values and said impendence values.

16. A method for measuring hemoglobin in whole blood with a sensor strip according to claim 1 that contains a blood sample in contact with the first and the second amounts of reagent composition, said method comprising:
applying amperometry and measuring current passing through the blood sample.

17. A method for measuring the hemoglobin content of a sample of whole blood, comprising:
introducing a hemoglobin sensitive redox mediator into said blood sample;
applying an initial electrical potential to said blood sample;
increasing said electrical potential in discrete steps until reaching an end electrical potential; and
measuring an electrical parameter of said whole blood after application of each electrical potential.

18. The method of claim 17, wherein said parameter comprises a current value.

19. The method of claim 17, wherein said parameter comprises a current value and further comprising measuring electrical impedance of said blood, wherein said current values and said impedance values are used together to obtain the hemoglobin content of said blood sample.

20. The method of claim 19, wherein using the current values and the impedance values together provide for measurement of hemoglobin content values over a linear range.

21. The method of claim 20, wherein the linear range is from at least 0 g/dL to 23 g/dL of hemoglobin.

22. The method of claim 17, wherein said initial potential is −0.5 volts, said end potential is 0.3 volts, and each discrete step is 0.1 volts per second.

23. The method of claim 17, wherein volume of said blood sample is in the range 1.6 micro liter to 10 micro liter.

24. A method for measuring the hemoglobin content of a sample of whole blood comprising:
introducing a hemoglobin sensitive redox mediator into said sample of whole blood;
obtaining an electrical current value for said sample of blood after said introducing step;
obtaining an impedance value for said blood sample after said introducing step;
multiplying said electrical current value with a first factor;
multiplying said impedance value with a second factor; and
adding the result of said first multiplication step to the result of said second multiplication; wherein said first factor and said second factor add up to one.

25. The method of claim 24, wherein volume of said blood sample is in the range of 1.6 micro liter to 10 micro liter.

26. The method of claim 24, wherein said redox mediator comprises a ferricyanide salt.

27. The method of claim 24, wherein said redox mediator comprises potassium ferricyanide.

28. A sensor strip configured for hemoglobin measurements in a whole blood sample, comprising:
a base layer having at least a first electrically conductive layer and a second electrically conductive layer disposed on a surface thereof;
a first amount of a reagent composition that includes at least an effective amount of a hemoglobin sensitive redox mediator and an effective amount of polymer binder in contact with said first electrically conductive layer to define a working electrode and a second amount of a reagent composition that includes an effective amount of polymer binder in contact with said second electrically conductive layer to define a reference electrode; and a channel providing communication between said first amount and said second amount of reagent composition;

wherein said sensor strip returns a measurable electrical signal indicative of the hemoglobin content of a blood sample having a volume in the range 1.6 micro liter to 10 micro liter in response to an application of voltage across said working electrode and said reference electrode when said blood sample is in contact with said first and second amounts of reagent composition inside said channel.

29. A method for measuring hematocrit content in a sample of whole blood comprising:

measuring the hemoglobin content of said whole blood sample using a sensor strip that includes a base layer having at least a first electrically conductive layer and a second electrically conductive layer disposed on a surface thereof;

a first amount of a reagent composition that includes at least an effective amount of a hemoglobin sensitive redox mediator in contact with said first electrically conductive layer to define a working electrode and a second amount of a reagent composition in contact with said second electrically conductive layer to define a reference electrode; and a channel providing communication between said first amount and said second amount of reagent composition;

wherein said sensor strip returns a measurable electrical signal indicative of the hemoglobin content of a blood sample in response to an independent application of a variable voltage and a constant voltage across said working electrode and said reference electrode when said blood sample is in contact with said first and second amount of reagent composition inside said channel;

determining the hematocrit content based on the measured hemoglobin content using a linear relationship of the form $$Hct = aHb + b$$

wherein Hct represents hematocrit content, Hb is the hemoglobin content and a and b are constants.

30. The method of claim 29, wherein the linear relationship is determined by measuring the hematocrit content of said whole blood using another method; and correlating the results of said first measurement step with said second measurement step to obtain the linear relationship indicative of the hematocrit content in said whole blood.

31. A sensor strip configured for hemoglobin measurements in a whole blood sample, comprising:

a base layer;

at least a first electrically conductive layer, a second electrically conductive layer, and a third electrically conductive layer on said base layer;

a first amount of a first reagent composition that includes at least an effective amount of a hemoglobin sensitive redox mediator in contact with said first electrically conductive layer to define a working electrode and a second amount of a second reagent composition in contact with said second electrically conductive layer to define a reference electrode;

a third reagent composition in contact with said third conductive layer to define a blank electrode, said third reagent composition including a hemoglobin insensitive redox mediator; and a channel providing communication between said first amount and said second amount of said reagent composition;

wherein said sensor strip returns a measurable electrical signal indicative of the hemoglobin content of a blood sample in response to an application of a voltage across said working electrode and said reference electrode when said blood sample is in contact with said first and second amount of said reagent composition inside said channel; wherein said measurable electrical signal is not influenced by the presence of an amount less than a maximum amount of an interfering oxidizable species.

32. The sensor strip of claim 31, wherein said maximum amount is determinable empirically by adding to a sample of whole blood different amounts of said interfering oxidizable species, measuring the current from said blank electrode and said working electrode after application of a voltage for each amount of added oxidizable species, determining a corrected current signal after each measurement of the current from said blank electrode and said working electrode based on a relationship having the form $$I = I2 - kI1$$

wherein I is the corrected signal proportional to hemoglobin content in said sample, I1 is the current value at said blank electrode, I2 is the current at the working electrode and k is a constant and comparing each determined corrected signal to a respective reference value to determine whether the added interfering oxidizable species has influenced said measurable electrical signal.

33. A method of measuring hemoglobin in whole blood using a sensor strip that includes a base layer; at least a first electrically conductive layer, a second electrically conductive layer, and a third electrically conductive layer on said base layer; a first amount of a reagent composition that includes at least an effective amount of a hemoglobin sensitive redox mediator in contact with said first electrically conductive layer to define a working electrode and a second amount of a second reagent composition in contact with said second electrically conductive layer to define a reference electrode; a third reagent composition in contact with said third conductive layer to define a blank electrode, said third reagent composition including a hemoglobin insensitive redox mediator; and a channel providing communication between said first amount and said second amount of said reagent composition; wherein said sensor strip returns a measurable electrical signal indicative of the hemoglobin content of a blood sample in response to an application of a voltage to said working electrode and said reference electrode when said blood sample is in contact with said first and second amount of said reagent composition inside said channel, the method comprising:

applying a first voltage across said blank electrode and said reference electrode for a first period of time;

applying a second voltage across said working electrode and said reference electrode for a second period of time; and after an open circuit delay for a third period of time, applying linear scan voltammetry across said working and reference electrodes in voltage increments from an initial voltage value to a final voltage value at a predetermined rate to determine electrical current values at the voltage increments; and determining the hemoglobin content from the peak current value obtained from application of said linear scan voltammetry.

34. The method of claim 33, wherein said first voltage is 0.7 Volts, said first period of time is five seconds, said second voltage is 1.0 Volt, said second period of time is 10 seconds, said third period of time is 17 seconds, said initial voltage value is −0.5 Volts, said final voltage value is 0.3 Volts, and said predetermined rate is 0.1 V/s.

35. A method of measuring hemoglobin in whole blood using a sensor strip that includes a base layer; at least a first electrically conductive layer, a second electrically conductive layer, and a third electrically conductive layer on said base layer; a first amount of a reagent composition that includes at least an effective amount of a hemoglobin sensitive redox mediator in contact with said first electrically conductive layer to define a working electrode and a second amount of a second reagent composition in contact with said second electrically conductive layer to define a reference electrode; a third reagent composition in contact with said third conductive layer to define a blank electrode, said third reagent composition including a hemoglobin insensitive redox mediator; and a channel providing communication between said first amount and said second amount of said reagent composition; wherein said sensor strip returns a measurable electrical signal indicative of the hemoglobin content of a blood sample in response to an application of a voltage across said working electrode and said reference electrode when said blood sample is in contact with said first and second amount of said reagent composition inside said channel, the method comprising:

applying a first voltage across said blank electrode and said reference electrode for a first period of time;

applying a second voltage across said working electrode and said reference electrode for a second period of time; and after an open circuit delay for a third period of time, applying a constant voltage while measuring the rise in current over time between said working and blank electrodes to determine the hemoglobin content.

36. The method of claim 35, wherein said first voltage is 0.7 Volts, said first period of time is five seconds, said second voltage is 1.0 Volts, said second period of time is 10 seconds, and said third period of time is 17 seconds while said circuit is open.

37. The sensor strip of claim 1, wherein said constant voltage is below a minimum voltage that would cause electrolysis of water.

38. The sensor strip of claim 37, wherein the constant voltage is 0.2 V.

39. The sensor strip of claim 1, wherein said first and second amounts of reagent composition are isolated from one another.

* * * * *